US012428648B2

(12) United States Patent
Tzanetakis et al.

(10) Patent No.: US 12,428,648 B2
(45) Date of Patent: *Sep. 30, 2025

(54) COMPOSITIONS COMPRISING PEPTIDES THAT BLOCK TRANSMISSION OF ORTHOTOSPOVIRUSES

(71) Applicant: THE BOARD OF TRUSTEES OF THE UNIVERSITY OF ARKANSAS, Little Rock, AR (US)

(72) Inventors: Ioannis Tzanetakis, Fayetteville, AR (US); Jing Zhou, Greenbelt, MD (US)

(73) Assignee: THE BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 137 days.

This patent is subject to a terminal disclaimer.

(21) Appl. No.: 18/117,995

(22) Filed: Mar. 6, 2023

(65) Prior Publication Data

US 2023/0365986 A1    Nov. 16, 2023

Related U.S. Application Data

(62) Division of application No. 16/913,721, filed on Jun. 26, 2020, now Pat. No. 11,597,945.

(60) Provisional application No. 62/866,855, filed on Jun. 26, 2019.

(51) Int. Cl.
*A61K 39/395*    (2006.01)
*C07K 7/08*    (2006.01)
*C12N 15/82*    (2006.01)

(52) U.S. Cl.
CPC ............ *C12N 15/8283* (2013.01); *C07K 7/08* (2013.01)

(58) Field of Classification Search
None
See application file for complete search history.

(56) References Cited

U.S. PATENT DOCUMENTS 11,597,945 B2 *    3/2023    Tzanetakis ........... C07K 14/005

OTHER PUBLICATIONS

Badillo-Vargas, I.E. et al. 2018. Discovery of novel thrips vector proteins that bind to the plant bunyavirus, tomato spotted wilt virus. bioRxiv 416560; doi: https://doi.org/10.1101/416560.
Badillo-Vargas, I.E. et al. 2014. Dissecting the molecular interplay between Tomato spotted wilt virus and the insect vector, Frankliniella occidentalis. Kansas State University, Manhattan, U.S.
Bai, M. et al. Mutations that alter an Arg-Gly-Asp (RGD) sequence in the adenovirus type 2 penton base protein abolish its cell-rounding activity and delay virus reproduction in flat cells. JJ Virol. Sep. 1993;67(9):5198-205. doi: 10.1128/JVI.67.9.5198-5205.1993.
Bellis, S.L. Advantages of RGD peptides for directing cell association with biomaterials. Biomaterials. Jun. 2011;32(18):4205-10. doi: 10.1016/j.biomaterials.2011.02.029.
Chen, T.C. et al. Molecular characterization of the full-length L and M RNAs of Tomato yellow ring virus, a member of the genus Tospovirus. Virus Genes. Jun. 2013;46(3):487-95. doi: 10.1007/s11262-013-0880-8. Epub Jan. 19, 2013. PMID: 23334441.
Gutiérrez-Rivas, M. et al. Tolerance to mutations in the foot-and-mouth disease virus integrin-binding RGD region is different in cultured cells and in vivo and depends on the capsid sequence context. J Gen Virol. Oct. 2008;89(Pt 10):2531-2539. doi: 10.1099/vir.0.2008/003194-0. PMID: 18796722.
Han, J. et al. Vector Competence of Thrips Species to Transmit Soybean Vein Necrosis Virus. Front Microbiol. Mar. 19, 2019;10:431. doi: 10.3389/fmicb.2019.00431. PMID: 30941106; PMCID: PMC6433834.
Haubner, R. et al. Structural and functional aspects of RGD-containing cyclic pentapeptides as highly potent and selective integrin alphavbeta3 antagonists. J. Am. Chem. Soc. 1996, 118(32):7461-7472.
Hersel, U. et al. RGD modified polymers: biomaterials for stimulated cell adhesion and beyond. Biomaterials. Nov. 2003;24(24):4385-415. doi: 10.1016/s0142-9612(03)00343-0. PMID: 12922151.
Keough, S. et al. Effects of Soybean Vein Necrosis Virus on Life History and Host Preference of Its Vector, Neohydatothrips variabilis, and Evaluation of Vector Status of Frankliniella tritici and Frankliniella fusca. J Econ Entomol. Oct. 2016;109(5):1979-87. doi: 10.1093/jee/tow145. Epub Jul. 14, 2016. PMID: 27417640.
Lin, H.B. et al. Synthesis, surface, and cell-adhesion properties of polyurethanes containing covalently grafted RGD-peptides. J Biomed Mater Res. Mar. 1994;28(3):329-42. doi: 10.1002/jbm.820280307. PMID: 8077248.
Liu, S. et al. A peptide that binds the pea aphid gut impedes entry of Pea enation mosaic virus into the aphid hemocoel. Virology. May 25, 2010;401(1):107-16. doi: 10.1016/j.virol.2010.02.009. Epub Mar. 11, 2010. PMID: 20223498.
Marsh, M. & Helenius, A. Virus entry: open sesame. Cell. Feb. 24, 2006;124(4):729-40. doi: 10.1016/j.cell.2006.02.007. PMID: 16497584; PMCID: PMC7112260.

(Continued)

*Primary Examiner* — Yunsoo Kim
(74) *Attorney, Agent, or Firm* — Quarles & Brady,LLP

(57) ABSTRACT

Orthotospovirus virions travel through the thrips foregut and enter midgut epithelial cells through the interaction between virus glycoproteins and cellular receptors with several protein motifs thought to be involved in the interaction. Single, double and triple mutant polypeptides in the soybean vein necrosis virus (SVNV)/*Neohydatothrips variabilis* system are provided herein and several are shown to block viral transmission from the thrips to the soybean plants. Methods for inhibiting viral transmission using these polypeptides or constructs comprising polynucleotides encoding peptides are also provided herein.

20 Claims, 9 Drawing Sheets
(8 of 9 Drawing Sheet(s) Filed in Color)
Specification includes a Sequence Listing.

(56) References Cited

OTHER PUBLICATIONS

Montero-Astúa, M. et al. Salivary gland morphology, tissue tropism and the progression of tospovirus infection in Frankliniella occidentalis. Virology. Jun. 2016;493:39-51. doi: 10.1016/j.virol.2016.03.003. Epub Mar. 21, 2016. PMID: 26999025.

Montero-Astúa, M. 2012. Ph.D dissertation. Unveiling and blocking the interaction between Tomato spotted wilt virus and its insect vector, Frankliniella occidentalis. Kansas State University, Manhattan, U. S.

Pierschbacher, M.D. & Ruoslahti, E. Cell attachment activity of fibronectin can be duplicated by small synthetic fragments of the molecule. Nature. May 3-9, 1984;309(5963):30-3. doi: 10.1038/309030a0. PMID: 6325925.

Pierschbacher, M.D. & Ruoslahti, E. Influence of stereochemistry of the sequence Arg-Gly-Asp-Xaa on binding specificity in cell adhesion. J Biol Chem. Dec. 25, 1987;262(36):17294-8. PMID: 3693352.

Plow, E.F. et al. Arginyl-glycyl-aspartic acid sequences and fibrinogen binding to platelets. Blood. Jul. 1987;70(1):110-5. PMID: 3036276.

Rotenberg, D. et al. Thrips transmission of tospoviruses. Curr Opin Virol. Dec. 2015;15:80-9. doi: 10.1016/j.coviro.2015.08.003. Epub Sep. 2, 2015. PMID: 26340723.

Schwab, E.H. et al. Distinct effects of RGD-glycoproteins on Integrin-mediated adhesion and osteogenic differentiation of human mesenchymal stem cells. Int J Med Sci. Nov. 9, 2013;10(13):1846-59. doi: 10.7150/ijms.6908. PMID: 24324361; PMCID: PMC3856375.

Ullman, D.E. et al. Thrips and tospoviruses come of age: mapping determinants of insect transmission. Proc Natl Acad Sci U S A. Apr. 5, 2005;102(14):4931-2. doi: 10.1073/pnas.0501341102. Epub Mar. 28, 2005. PMID: 15795369; PMCID: PMC555985.

Wei, Y. et al. Roles of the putative integrin-binding motif of the human metapneumovirus fusion (f) protein in cell-cell fusion, viral infectivity, and pathogenesis. J Virol. Apr. 2014;88(8):4338-52. doi: 10.1128/JVI.03491-13. Epub Jan. 29, 2014. PMID: 24478423; PMCID: PMC3993731.

Whitfield, A.E. et al. Insect vector-mediated transmission of plant viruses. Virology. May 2015;479-480:278-89. doi: 10.1016/j.virol. 2015.03.026. Epub Mar. 29, 2015. PMID: 25824478.

Whitfield, A.E. et al. A soluble form of the Tomato spotted wilt virus (TSWV) glycoprotein G(N) (G(N)-S) inhibits transmission of TSWV by Frankliniella occidentalis. Phytopathology. Jan. 2008;98(1):45-50. doi: 10.1094/PHYTO-98-1-0045. PMID: 18943237.

Whitfield, A.E. 2004. Ph.D dissertation. Tomato spotted wilt virus acquisition by thrips: the role of the viral glycoproteins. University of Wisconsin-Madison, Madison, U. S.

Whitfield, A.E. et al. Tospovirus-thrips interaction. Annu Rev Phytopathol. 2005;43:459-89. doi: 10.1146/annurev.phyto.43.040204. 140017. PMID: 16078892.

Whitfield, A.E. et al. Expression and characterization of a soluble form of Tomato spotted wilt virus glycoprotein GN. J Virol. Dec. 2004;78(23):13197-206. doi: 10.1128/JVI.78.23.13197-13206. 2004. PMID: 15542672; PMCID: PMC524983.

Yu, Y-P. et al. Molecular basis for the targeted binding of RGD-contain peptide to integrin $\alpha V\beta 3$. Biomaterials. Feb. 2014;35(5):1667-75. doi: 10.1016/j.biomaterials.2013.10.072. Epub Nov. 20, 2013. PMID: 24268666.

Zhou, J. et al. Molecular characterization of a new Tospovirus infecting soybean. Virus Genes. Oct. 2011;43(2):289-95. doi: 10.1007/s11262-011-0621-9. Epub May 22, 2011. PMID: 21604150.

Office Action for U.S. Appl. No. 16/913,721, mailed Jan. 20, 2022.

Restriction Requirement for U.S. Appl. No. 16/913,721 mailed Aug. 11, 2021.

Zhou, J. & Tzanetakis, I.E. Transmission blockage of an orthotospovirus using synthetic peptides. J Gen Virol. Jan. 2020;101(1):112-121. doi: 10.1099/jgv.0.001352. PMID: 31724933.

\* cited by examiner a RNA 1 – 9010 nt

RNA-dependant RNA-polymerase

RNA 2 – 4955 nt non-structural protein

NSm  Glycoprotein precursor

Gn | Gc

RNA 3 – 2603 nt non-structural protein

NSs

Nucleoprotein b

Gn　　　　　　　　　　Gc $RGD_{78-81}$ $N_{25}$　　　　　$N_{229}$　　　　$N_{343}$

COMPOSITIONS COMPRISING PEPTIDES THAT BLOCK TRANSMISSION OF ORTHOTOSPOVIRUSES

CROSS-REFERENCE TO RELATED APPLICATIONS

This application is a divisional of U.S. patent application Ser. No. 16/913,721, filed Jun. 26, 2020, and issued as U.S. Pat. No. 11,597,945, which claims priority to U.S. Provisional Patent Application No. 62/866,855, filed Jun. 26, 2019, each of which is incorporated herein by reference in its entirety for all purposes.

STATEMENT REGARDING FEDERALLY FUNDED RESEARCH OR DEVELOPMENT

This invention was made with government support under Grant No. EPS-1003970 awarded by the US National Science Foundation. The government has certain rights in the invention.

REFERENCE TO A SEQUENCE LISTING SUBMITTED VIA PATENT CENTER

A sequence listing XML named "169946.00709_ST26.xml", which is 14,576 bytes in size and was created on Jun. 20, 2023, is electronically submitted via Patent Center herewith. The sequence listing is incorporated herein by reference in its entirety.

INTRODUCTION

Orthotospoviruses are plant viruses that have significant economic impact in global agriculture and are solely transmitted by thrips in nature. Thrips (order Thysanoptera) are the only known vectors of orthotospoviruses, (Pappu et al., 2009; Oliver and Whitfield, 2016). There are more than 5500 thrips species described to date and 17, belonging to the genera *Frankliniella, Thrips, Ceratothripoides, Scirtothrips*, *Dictyothrips, Neohydatothrips* and *Taeniothrips*, are confirmed orthotospovirus vectors (Riley et al., 2011; Montero-Astúa, 2012; Xu et al., 2017; Zhou and Tzanetakis, 2019). The interactions between tomato spotted wilt virus (TSWV)—the type member of the genus and its primary vector—*Frankliniella occidentalis* have been extensively studied and the results have shed light on important attributes of thrips-orthotospovirus interactions (Rotenberg et al., 2015; Whitfield et al., 2015).

Virions are acquired by thrips through piercing and sucking on epidermal and mesophyll cells of infected leaflets and subsequently travel from stylet through the foregut before reaching the midgut where virus replication occurs (Montero-Astúa, 2012; Badillo-Vargas, 2014). New transmission event occurs when thrips eject viruses into another host during feeding (Whitfield et al., 2005; Montero-Astúa, 2012; Badillo-Vargas, 2014).

SUMMARY

The present work is directed to a series of polypeptides that satisfies the need of providing antiviral compounds that block transmission of the virus from the larvae to the plant. The presented polypeptides comprise single, double and triple amino acid mutations at the $RGD_{29\text{-}31}$ site and $N_{229}$ site of glycoprotein N. The effects on viral transmission by these polypeptides are demonstrated.

The work presented here includes a series of synthesized peptides derived from glycoprotein N of SVNV that block the transmission of the virus through soybean thrips to plants. These peptides could be incorporated into either soybean plants to generate SVNV-resistant/tolerant accessions or into chemicals targeting soybean thrips to minimize the spread of SVNV through the vector.

In one aspect, polypeptides designed around the $RGD_{29\text{-}31}$ domain and $Asn_{229}$ of glycoprotein N of SVNV are shown to inhibit viral transmission. These peptides include SEQ ID NO: 1-6, and polypeptides having at least 80, 85, 90, 95, 98, and 99% identity to these polypeptides. Compositions comprising combinations of these peptides are also provided herein.

In another aspect, the polynucleotides encoding the polypeptides provided herein are provided. These polynucleotides may be used in constructs, such as expression constructs. The constructs may include a promoter operably connected to the polynucleotides to allow for the expression of the polynucleotides and production of the polypeptides provided herein in a cell, larvae, or plant.

In another aspect, transgenic or otherwise genetically modified plants comprising the constructs or the polynucleotides encoding the polypeptides are provided. The transgenic cells may be plant cells and may be part of a transgenic plant. Seeds, parts, progeny and asexual propagates of the transgenic plants are also provided. In another aspect, a non-transgenic plant comprising the polypeptides, the constructs or the polynucleotides encoding the polypeptides are provided.

In yet another aspect, methods for inhibiting viral transmission comprising contacting larvae with the polypeptides of SEQ ID NOs: 1-6, polynucleotides encoding the polypeptides of SEQ ID NOs: 1-6 or by the constructs comprising polynucleotides encoding the polypeptides operably connected to a promoter or by contacting larvae with the transgenic or non-transgenic plants mentioned above are provided.

In another aspect, methods of inhibiting viral transmission by administering the polypeptides of SEQ ID NOs: 1-6 to a plant are provided.

In another aspect, methods of inhibiting viral transmission by administering the polypeptides of SEQ ID NO: 1-6, polynucleotides encoding the polypeptides of SEQ ID NOs: 1-6 or the constructs, or plants mentioned above to larvae are provided.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

These and other features, aspects, and advantages of the present invention will become better understood with regard to the following description, appended claims, and accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 shows (a) a Soybean vein necrosis virus (SVNV) genome diagram and (b) a schematic representation of the RGD motif, N-glycosylation sites and transmembrane domains on glycoprotein N.

FIG. 3 shows (a) a comparison of mean feeding rates between thrips fed with buffer, buffer/SVNV and SVNV alone, respectively (P>0.05), and (b) a comparison of mean infection rates between thrips fed with buffer, buffer/SVNV and SVNV alone, respectively (P<0.0001).

DETAILED DESCRIPTION

Figure 2:
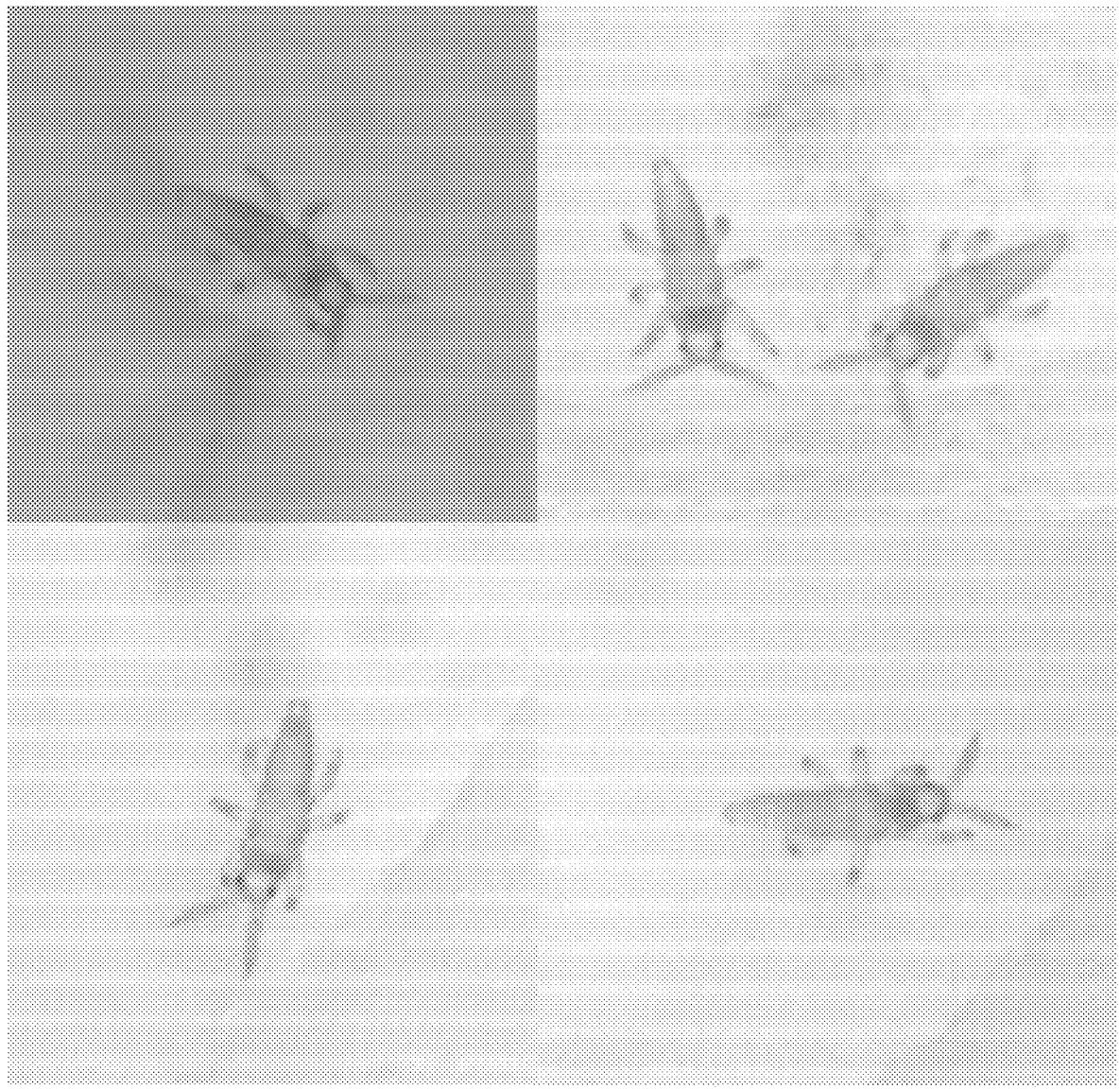
FIG. 2 demonstrates the successful peptide delivery to larvae. First instar larvae that has successfully acquired (first row) or failed to acquire (second row) peptide solution. A homogeneous blue color observed through the abdomen of the larvae after feeding with peptide solution was used as an indicator of successful peptide delivery and only blue larvae were harvested and used for downstream experiments.

Studies performed by Whitfield et al. (2004) proved that a recombinant, soluble form of TSWV glycoprotein N ($G_N$) binds to larval thrips guts and decreases virus acquisition, providing evidence that $G_N$ protein is crucial in mediating the attachment of virion to receptors displayed on the epithelial cells of the thrips midgut. $G_N$ along with the $G_C$ glycoprotein play essential roles in virus entry into host cells (Whitfield et al., 2005; Ullman et al., 2015). Sequence analysis of the soybean vein necrosis virus (SVNV) $G_N$ protein revealed the presence of an $RGD_{29-31}$ motif, the characteristic of cell adhesion molecules.

The $G_N$ protein is a good candidate for antiviral compounds given that its soluble form generated by Whitfield et al. (2004) bound to thrips guts and inhibited TSWV transmission (Whitfield et al., 2008). Apart from utilizing recombinant proteins, synthetic peptide targeting key sequences or motifs of viral proteins is a promising strategy used to reduce virus transmission as demonstrated in both plant and animal virus interactions (Wild et al., 1992; Santos et al., 2002; Firbas et al., 2006; Liu et al., 2010; Borrego et al., 2013; Muhamad et al., 2015; Yang et al., 2017).

The RGD motif is present in SVNV and several other orthotospoviruses belonging to the American clade of the genus (Chen et al., 2013). Its function in virus attachment/entry to thrips midgut cells and the potential effect of this interaction on transmission of orthotospoviruses, however, is not understood.

The inventors have surprisingly found that peptides derived from the glycoprotein N of SVNV can inhibit the transmission of the SVNV virus from the thrips to soybean plants. The peptides having mutations within the RGD domain were some of the peptides with the highest percent inhibition of viral transmission which was very unexpected. Several of the peptides were more effective when used in combination. Thus provided herein are polypeptides capable of inhibiting viral transmission from the larvae to the plants when used alone or in combination in a composition comprising combinations of peptides. Constructs including polynucleotides encoding modified polypeptides of the RGD domain or including the N-glycosylation site of the soybean vein necrosis virus (SVNV) $G_N$ protein are provided herein as SEQ ID NOs: 1-6. These peptides were demonstrated to inhibit viral transmission from the larvae to the plants. In addition, methods of inhibiting viral transmission to plants by contacting larvae with the polypeptides of SEQ ID NOs: 1-6, or by contacting larvae with polynucleotides or by contacting larvae with constructs containing polynucleotides encoding these polypeptides are provided herein. Methods of inhibiting viral transmission by administering the polypeptides of SEQ ID NOs: 1-6 to a plant are also provided as well as methods of inhibiting viral transmission by administering the polypeptides of SEQ ID NOs: 1-6 or polynucleotides encoding the peptides or constructs or transgenic plants including the peptides or polynucleotides to thrips larvae are provided herein. Transgenic plants or transgenic plant cells that inhibit viral transmission and which carry a transgene encoding a non-native or exogenous derived polynucleotide encoding at least one of the polypeptides of SEQ ID NOs: 1-6 are provided herein. Non-transgenic, non-naturally occurring plants carrying the polypeptides or bred or otherwise engineered to express the polypeptides or the polynucleotides encoding the polypeptides are also disclosed. Methods of inhibiting viral transmission by administering transgenic plants or non-transgenic plants to larvae are also provided herein.

Orthotospoviruses are plant viruses that have significant economic impact in global agriculture and are solely transmitted by thrips in nature. Peptides that inhibit the transmission of orthotospoviruses from thrips into plants are presented herein. These peptides may be delivered to the thrips via many ways that may be apparent to those skilled in the art including via feeding on a plant expressing the polypeptide or drinking water spiked with the peptides.

Thrips (order Thysanoptera) are the only known vectors of orthotospoviruses, viruses that cause significant economic losses globally (Pappu et al., 2009; Oliver and Whitfield, 2016). There are more than 5500 thrips species described to date and 17, belonging to the genera *Frankliniella, Thrips, Ceratothripoides, Scirtothrips, Dictyothrips, Neohydatothrips* and *Taeniothrips*, are confirmed orthotospovirus vectors (Riley et al., 2011; Montero-Astúa, 2012; Xu et al., 2017; Zhou and Tzanetakis, 2019). Thrips develop resistance to insecticides easily and there is constant research for additional methods to control them. Due to their small sizes and high rates of reproduction, thrips are difficult to control using classical biological control means. Suitable predators must be small and slender enough to penetrate the crevices where thrips hide while feeding, and they must also prey extensively on eggs and larvae to be effective.

As used herein, thrips (order Thysanoptera) are the only known vectors of orthotospoviruses. Examples of these vectors include, but are not limited to, *Ceratothripoides claratris, T. palmi, F. schultzei, F. occidentalis, F. schultzei, F. occidentalis, F. intonsa, F. gemina, F. intonsa, T. tabaci, T. palmi, Scirtothrips dorsalis, F. fusca, F. bispinosa, T. setosus, F. zucchini, Microcephalothrips abdominalis,* and thrips belonging to the genera *Frankliniella, Thrips, Ceratothripoides, Scirtothrips, Dictyothrips, Neohydatothrips,* and *Taeniothrips.*

The interactions between tomato spotted wilt virus (TSWV)—the type member of the genus and its primary vector—*Frankliniella occidentalis* have been extensively studied and the results have shed light on important attributes of thrips-orthotospovirus interactions (Rotenberg et al., 2015; Whitfield et al., 2015). Virus transmission occurs in a persistent propagative manner, transtadially but not transovarially. Although virions can be acquired by thrips throughout their lifetime, only the individuals that ingest viruses in the first and early second instars stages are capable of transmitting the virus to the plants (Ullman et al., 2005; Whitfield et al., 2005). It is well understood in the art that instar stage can be used interchangeably with larva or larva stage and refers to the developmental stage of arthropods.

Orthotospoviruses or tospoviruses are used interchangeably and refer to viruses of the genus Orthotospovirus, family Tospoviridae. Examples of these viruses include, but are not limited to, tomato spotted wilt virus (TSWV), soybean vein necrosis virus (SVNV), impatiens necrotic spot virus (INSV), bean necrotic mosaic virus (BNMV), capsicum chlorosis virus (CaCV), calla lily chlorotic spot virus (CCSV), chrysanthemum stem necrosis virus (CSNV), groundnut ringspot virus (GRSV), groundnut bud necrosis virus (GBNV), groundnut yellow spot virus (GYSV), iris yellow spot virus (IYSV), melon yellow spot virus (MYSV), peanut bud necrosis virus (PBNV), peanut chlorotic fan virus (PCFV), peanut yellow spot virus (PYSV), tomato chlorotic spot virus (TCSV), tomato yellow fruit ring virus (TYFRV) (=ToVV, tomato varamin virus), tomato necrotic ringspot virus (TNRV), tomato yellow ring virus (TYRV), tomato zonate spot virus (TZSV), watermelon bud necrosis virus (WBNV), watermelon silver mottle virus (WSMoV), zucchini lethal chlorosis tospovirus (ZLCV), polygonum ringspot virus (PolRSV), hippeastrum chlorotic ringspot virus (HCRV), melon yellow spot virus (MYSV), pepper chlorotic spot virus (PCSV), tomato necrotic spot associated virus (TNSaV), groundnut chlorotic fan-spot virus (GCFSV), mulberry vein banding associated virus (MVBaV), chilli yellow ringspot virus (ChiYRSV).

Virions are acquired by thrips through piercing and sucking on epidermal and mesophyll cells of infected leaflets and subsequently travel from stylet through the foregut before reaching the midgut where virus replication occurs (Montero-Astúa, 2012; Badillo-Vargas, 2014). Several models have been proposed for virus movement in thrips; the generally accepted one suggests that viruses enter midgut epithelium cells through receptor-mediated endocytosis which involves the interaction between viral glycoproteins and cellular receptors. Following entry, virus replication occurs in the cytoplasm. Virus progeny are released from infected cells through shedding and move across midgut microvilli, basal surface of epithelial cells and muscle cells surrounding basal membranes. Once virions leave the last membrane barrier of muscle cells, they traverse basal membrane and microvilli of the salivary gland, the critical organ in virus transmission, and move with saliva into a canal leading to an efferent salivary and exit from the combined salivary-food canal. New transmission events occur when thrips eject viruses into another host during feeding (Whitfield et al., 2005; Montero-Astúa, 2012; Badillo-Vargas, 2014). Virions are commonly referred to as the entire virus particle or structure.

Virus transmission or viral transmission or virus infection are used interchangeably and refer to the transfer of a virus to a plant via thrips. As used herein, viral transmission also refers to the thrips acquisition of a plant virus by piercing and sucking on cells of infected leaflets and then thrips transmit the virus to another plant host when feeding on the uninfected plant.

Entry into host cells is the early step in the virus infection process. It is likely that virions are engulfed into host cells through receptor-mediated endocytosis, a common entry mechanism utilized by enveloped viruses (Whitfield et al., 2005). This process involves a series of events; initiated by virion attachment to cellular receptors and culminating with the fusion between viral and host membranes (Ullman et al., 2005; Marsh and Helenius, 2006). Studies performed by Whitfield et al. (2004) proved that a recombinant, soluble form of TSWV glycoprotein N ($G_N$) binds to larval thrips guts and decreases virus acquisition, providing evidence that $G_N$ protein is crucial in mediating the attachment of virion to receptors displayed on the epithelial cells of the thrips midgut. $G_N$ along with the $G_C$ glycoprotein play essential roles in virus entry into host cells (Whitfield et al., 2005; Ullman et al., 2015). Sequence analysis of the soybean vein necrosis virus (SVNV) $G_N$ protein revealed the presence of an $RGD_{29-31}$ motif, characteristic of cell adhesion molecules. This motif binds specifically to integrins, a large family of transmembrane proteins consisting of non-covalently bound heterodimeric subunits. The integrins bind the RGD containing proteins through electrostatic interactions between the RGD residues and metal ions in integrins (Schwab et al., 2013; Badillo-Vargas, 2014; Yu et al., 2014). In addition, the N-linked glycosylation sites on the $G_N$ protein ($N_{25}$, $N_{229}$ and $N_{343}$ for SVNV) may also be involved in virus entry (Whitfield, 2004).

Host cells refer to plants or plant cells that can be infected by orthotospoviruses. A plant includes any portion of the plant including, but not limited to, a whole plant, a portion of a plant such as a root, leaf, stem, seed, pod, flower, cell, tissue or plant germplasm or any progeny thereof. Germplasm refers to genetic material from an individual or group of individuals or a clone derived from a line, cultivar, variety or culture. Plant refers to whole plants or portions thereof including, but not limited to, plant cells, plant protoplasts, plant tissue culture cells, leaves, root, stem, or calli. For example, soybean plant refers to whole soybean plant, or portions thereof including, but not limited, to, soybean plant cells, soybean plant protoplasts, soybean plant tissue culture cells or calli. A plant cell refers to cells harvested or derived from any portion of the plant or plant tissue culture cells or calli.

While soybean and SVNV are described specifically in the Examples, the orthotospoviruses are a large family of similar viruses that infect a wide variety of plants and use many different insect vectors. The inventors expect that all the orthotospoviruses with a similar glycoprotein N will also be inhibited from transmission to their plant hosts using the peptides described herein. Other examples of these plants include, but are not limited to, plants of the families: Acanthaceae, Aceraceae, Agavaceae, Aizoaceae, Alstroemeriaceae, Amaranthaceae, Amaryllidaceae, Apiaceae, Apocynaceae, Aquifoliaceae, Araceae, Araliaceae, Arecaceae, Aristolochiaceae, Asclepiadaceae, Asparagaceae, Asteraceae, Balsaminaceae, Begoniaceae, Berberidaceae, Boranginaceae, Brassicaceae, Bromeliaceae, Buxaceae, Cactaceae, Calectasiaceae, Calycanthaceae, Campanulaceae, Cannaceae, Capparaceae, Caprifoliaceae, Caricaceae, Caryophyllaceae, Chenopodiaceae, Commelinaceae, Convallariaceae, Convolvulaceae, Crassulaceae, Cuscutaceae, Cycadaceae, Cyperaceae, Dipsacaceae, Dracaenaceae, Dryopteridaceae, Ericaceae, Euphorbiaceae, Fabaceae, Fumariaceae, Gentianaceae, Geraniaceae, Gesneriaceae, Goodeniaceae, Greyiaceae, Haemodoraceae, Hydrangeaceae, Hydrocotylaceae (Apiaceae), Iridaceae, Labiatae, Lamiaceae, Liliaceae, Linaceae, Lobeliaceae, Loganiaceae, Magnoliaceae, Malvaceae, Marantaceae, Martyniaceae, Melastomataceae, Moraceae, Myrsinaceae, Myrtaceae, Nyctaginaceae, Oleaceae, Onagraceae, Orchidaceae, Oxalidaceae, Paeoniaceae, Papaveraceae, Pedaliaceae, Peperomiaceae, Phytolaccaceae, Plantaginaceae, Plumbaginaceae, Poaceae, Polemonaceae, Polygalaceae, Polygonaceae, Polypodiaceae, Portulacaceae, Primulaceae, Pteridaceae, Ranunculaceae, Rosaceae, Rubiaceae, Ruscaceae, Saxifragaceae, Scrophulariaceae, Solanaceae, Styracaceae, Tetragoniaceae, Theaceae, Tropaeolaceae, Ulmaceae, Urticaceae, Valerianaceae, Verbenaceae, Violaceae, and Zygophyllaceae.

Antiviral or viral inhibition or inhibition of viral transmission are used interchangeably and may refer to either the reduction of virus transmission from infected plant to vector (thrips) or the reduction of virus transmission from thrips carrying the virus to an uninfected plant or plant cell. Viral Inhibition may also refer to, but is not limited to, the interference with virus release from the vector, interference with virus entry into the host, interference with virus entry into the vector, interference with virus replication in the host, and interference with virus replication in the vector. Effective measurement of inhibition can be analyzed in the post hoc test using methods well known in the art such as, but not limited to, JMP Pro 13 (SAS Institute Inc., Cary, NC) and Dunnett's method (Dunnett, 1955). Lower infection rates may refer to infection rates having a P value of ≤0.05. Inhibition of viral transmission can also be assessed as a reduced infection rate or reduction in the percentage of plants which are infected after exposure to the vector comprising the virus as was done in the Examples provided herein. The peptides provided herein may reduce viral transmission or reduce the infection rate by 5%, 10%, 15%, 20% or more.

The RGD motif is present in SVNV and several other orthotospoviruses belonging to the American clade of the genus (Chen et al., 2013). Its function in virus attachment/entry to thrips midgut cells and the potential effect of this interaction on transmission of orthotospoviruses, however, is not well-understood. We hypothesized that the RGD motif as well as the N-linked glycosylation site of the SVNV $G_N$ protein ($N_{229}$ based on in-silico simulations) are critical in the early steps of virus infection process, and will decrease transmission efficiency when receptors are saturated with ligands prior to acquisition.

The usage of synthetic peptides as therapeutic agents has been explored in treating animal and human viral diseases (Houimel and Dellagi, 2009; Arosio et al., 2012; Gosselet et al., 2013; Hipolito et al., 2014; Muhamad et al., 2015; Zhang et al, 2015) while their application in controlling plant-infecting viruses is still in its infancy. To date, peptides that confer disease resistance are primarily interfering with viral proteins either associated with replication such as the nucleoprotein of orthotospoviruses and the replicase of geminivirus (Rudolph et al., 2003; Lopez-Ochoa et al., 2006) or virion assembly as seen with luteoviruses (Liu et al., 2010). Although Liu et al. (2010) identified a peptide inhibiting transmission of luteoviruses through impeding entry of virions into aphid hemocoel, the potential of utilizing peptides to block persistent, propagative-transmitted viruses is yet to be studied. Thus, this invention represents a new area for the use of peptides, namely to block transmission of orthotospoviruses.

It has been shown that $G_N$ protein of TSWV is the candidate target for antiviral compounds (Whitfield et al., 2004; Whitfield et al., 2008) and the cellular adhesion hallmark-RGD motif is predicted to be critical in virion attachment. The role of this motif in the orthotospovirus infection process and whether it could serve as a potential target of antiviral compound were unknown. The motif has been identified in $G_N$ proteins of several members in the genus of Orthotospovirus including SVNV, a distinct species transmitted by an uncommon vector N. variabilis. This orthotospovirus-thrips interaction may reflect unique transmission properties that are critical in the co-evolution of orthotopoviruses and their vectors. Here we designed polypeptides containing sequences of interest ($RGD_{29-31}$ and $Asn_{229}$) and the mutated forms of these sequences. By comparing transmission efficiency of N. variabilis fed with either single peptide or peptide combinations prior to virus acquisition, we found intriguing results which suggest peptides derived from RGD motif could be useful to decrease the transmission rate of SVNV.

In one embodiment, we developed peptides with single, double and triple amino acids mutations at the $RGD_{29-31}$ site and $N_{229}$ using alanine scanning and evaluated their effect on viral transmission. These polypeptides are shown in Table 1 as SEQ ID NO: 1-10 and encompass SEQ ID NOs: 1-6 which were demonstrated to be effective in blocking viral transmission. The highly related peptides of SEQ ID NO: 7-10 were shown to not be effective in blocking viral transmission. Polypeptides having 90% sequence identity to one of SEQ ID NOs: 1-6 are also provided. Polynucleotides encoding the polypeptides of SEQ ID NOs: 1-6 and constructs comprising the polynucleotides encoding the polypeptides of SEQ ID NOs: 1-6 operably connected to a heterologous promoter are also described herein. Combinations of the polypeptides and the polynucleotides may also be used. As shown in the Examples, combinations of some of the polypeptides were shown to significantly inhibit viral infection and transmission. The polypeptides and polynucleotides may be fused to form fusion polynucleotides and fusion proteins or may be simply combined in a unitary composition.

TABLE 1

Name and Sequences of Synthesized Peptides

| Peptide name | Mutation status | Sequence |
|---|---|---|
| RGD | Wild type | NASIRGDHEVSQE (SEQ ID NO: 1) |
| $N_{229}$ | Wild type | RLTGECNITKVSLTN (SEQ ID NO: 2) |
| AGD | Single mutation | NASIAGDHEVSQE (SEQ ID NO: 4) |
| RAD | Single mutation | NASIRADHEVSQE (SEQ ID NO: 5) |
| RGA | Single mutation | NASIRGAHEVSQE (SEQ ID NO: 6) |
| $A_{229}$ | Single mutation | RLTGECAITKVSLTN (SEQ ID NO: 7) |

TABLE 1-continued

Name and Sequences of Synthesized Peptides

| Peptide name | Mutation status | Sequence |
|---|---|---|
| AAD | Double mutation | NASIAADHEVSQE (SEQ ID NO: 8) |
| AGA | Double mutation | NASIAGAHEVSQE (SEQ ID NO: 9) |
| RAA | Double mutation | NASIRAAHEVSQE (SEQ ID NO: 10) |
| AAA | Triple mutation | NASIAAAHEVSQE (SEQ ID NO: 3) |

The terms polypeptide, peptide, and protein are known in the art and are used interchangeably to refer to a polymer of amino acid residues. The term also applies to amino acid polymers which contain one or more amino acids that are chemical analogs or modified derivatives of a corresponding naturally-occurring amino acids. Peptides modified to increase stability or resistance to proteases are also encompassed.

The terms polynucleotide or nucleotide can be used interchangeably to refer to a deoxyribonucleotide or a ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties. In general, an analogue of a particular nucleotide has the same base-pairing specificity; i.e., an analogue of G will base-pair with C.

A sequence refers to an amino acid sequence or a nucleotide sequence of any length, which can be DNA or RNA or protein; can be linear, circular or branched and can be either single-stranded or double-stranded. While sequence identity refers to an exact nucleotide-to-nucleotide or amino acid-to-amino acid correspondence of two polynucleotides or polypeptide sequences, respectively. Techniques for determining nucleic acid and amino acid sequence identity are known in the art. Two or more sequences can be compared by determining their percent identity. The percent identity is the number of exact matches between two aligned sequences divided by the length of the shorter sequences and multiplied by 100. With respect to sequences described herein, the range of desired degrees of sequence identity is approximately 80% to 100% and any integer value there between. Typically, the percent identities between sequences are at least 70-75%, preferably 80-82%, more preferably 85-90%, even more preferably 92%, still more preferably 95%, and most preferably 98% sequence identity.

A construct refers to an artificially constructed segment of nucleic acid that is to be transplanted into a target tissue or cell. The construct generally consists of a promoter sequence, followed by a desired gene, and ends in a transcription termination or polyadenylation signal sequence. The construct may contain an insert, which contains a gene sequence encoding a protein of interest that has been subcloned into a vector. The vector or construct also often contains resistance or other marker genes for growth in sensitive cells or selection of cells containing the construct or vector, and promoters for expression in the organism. A construct may express wild-type protein, prevent the expression of certain genes by expressing competitors or inhibitors, express mutant proteins or carry and allow for expression of non-native proteins.

When referring to heterologous, we refer to a molecule that is not normally present in a cell, but can be introduced into a cell by one or more genetic, biochemical, or other methods. A heterologous molecule can be, among other things, a small molecule such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. A heterologous promoter is a promoter that is not operably connected to a gene under normal or wild-type conditions, but is being used to drive expression of the gene. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer.

The term promoter includes reference to a region of DNA generally upstream from the start of transcription and involved in recognition and binding of RNA polymerase and other proteins to initiate transcription. A plant-specific promoter is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as tissue preferred. Promoters which initiate transcription only in certain tissue are referred to as tissue specific. A cell-specific promoter primarily drives expression in certain cell types in one or more organs, for example, vascular cells in roots or leaves. An inducible promoter is a promoter which is under environmental control. Examples of environmental conditions that may affect transcription by inducible promoters include anaerobic conditions or the presence of light. Tissue specific, tissue preferred, cell specific, and inducible promoters constitute the class of non-constitutive promoters. A constitutive promoter is a promoter which is active under most environmental conditions.

Also provided herein are constructs including a promoter operably linked to a polynucleotide encoding the polypeptides comprising SEQ ID NOs: 1-6 or a fragment or functional variant thereof or a fusion product including at least one of SEQ ID NOs: 1-6. The constructs may be introduced into plants to make transgenic plants or may be introduced into plants, or portions of plants, such as plant tissue, plant calli, plant roots or plant cells. Suitably the promoter is a plant promoter, suitably the promoter is operational in leaf cells, seed, root or fruit cells or other tissues of the plant. The promoter may be tissue specific, inducible, constitutive, or developmentally regulated. The constructs may be an expression vector or a targeting vector for incorporation of the construct or a portion thereof into the cell. Constructs may be used to generate transgenic plants or transgenic cells. The polypeptide may be at least 80%, 85%, 90%, 95%, 97%, 98%, 99% or 100% identical to the sequences of SEQ ID NOs: 1-6. The constructs may comprise more than one polynucleotide and may mediate expression of one or more polypeptides or may comprise only one, two, three or more of the polynucleotides encoding the polypeptides provided herein or other polypeptides of interest.

In another embodiment, methods that prevent virus transmission by blocking virion entry into thrips cells or subsequent entry from the thrips into plant cells are provided herein. In another embodiment, methods that inhibit viral transmission by contacting larvae with the designed polypeptides of SEQ ID NOs: 1-6 are provided herein.

Contacting as used herein refers to the state or condition of physical touching and can refer to being in direct contact or touch, being in proximity, or being exposed to. As such, contacting may mean exposing larvae to the polypeptides of SEQ ID NOs: 1-6, exposing larvae to the constructs containing the polynucleotides encoding the polypeptides of SEQ ID NOs: 1-6, or exposing larvae to a transgenic plant, genetically-modified plant, or a non-genetically modified plant. Contacting the thrips with the compositions described herein may be via inclusion in the food or water the thrips are ingesting. For example, the polypeptides may be expressed in a plant or may be coated onto a plant such that when the larva feed on the plant the larvae are ingesting the polypeptides described herein. Genetically-modified plants or genetically-modified plant cells may refer to plants or plant cells that inhibit viral transmission by carrying a transgene encoding a polynucleotide encoding the polypeptides of SEQ ID NOs: 1-6. Transgenic plants or transgenic plant cells may refer to plants or plant cells that inhibit viral transmission by carrying a transgene or otherwise encoding a non-native or exogenous derived polynucleotide encoding the polypeptides of SEQ ID NOs: 1-6.

Administering may mean feeding the polypeptides of SEQ ID NOs: 1-6 to larvae, feeding the constructs containing the polynucleotides encoding the polypeptides of SEQ ID NOs: 1-6 to larvae, or feeding a transgenic plant, genetically-modified plant, or a non-genetically modified plant expressing SEQ ID NOs: 1-6 to larvae. It may also mean introducing the polypeptides of SEQ ID NOs: 1-6 or the constructs containing the polynucleotides encoding the polypeptides of SEQ ID NOs: 1-6 to a plant by common methods used in the art such as, but not limited to, spraying, inclusion of the polypeptides or constructs in the soil, inclusion of the polypeptides or constructs in fertilizers, and inclusion of the polypeptides or constructs to the soil.

Experiments illustrate the high SVNV transmission efficiency with single thrips (above 36%; Table 2). Because of this fact and in order to control virus dispersal, it is imperative to develop strategies that could block virion entry into thrips cells. In our experiments, transmission rates did not differ between thrips fed on buffer prior to virus acquisition and those fed only on SVNV tissue (P=1.00) indicating that the feeding solution does not interfere with transmission. The addition of blue food dye in the buffer not only attracts larvae to feed on solutions containing polypeptides but also enables us to visualize the acquisition status of the mixture. Survival rates of larvae did not differ from groups fed on the buffer and those that did not.

The transmission efficiency of SVNV by individual *N. variabilis* is over 36%, underlining the importance of disrupting virus-thrips interaction for effective virus control. The analysis of transmission efficiency mediated by synthetic polypeptides revealed that peptides derived from $RGD_{29-31}$ and $N_{229}$ motifs of the viral glycoprotein had the potential of blocking virion attachment to cellular receptors and consequently decreasing virus transmission efficiency. Surprisingly, one of the mutant peptides in which the RGD motif was replaced with Alanines demonstrated the best viral inhibition of all of the peptides tested to date. The mechanism by which this inhibition occurs is as yet unknown. This peptide was the only peptide that inhibited viral transmission significantly when used on its own.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 0.01% to 5%, it is intended that values such as 0.025% to 0.50%, 0.10% to 1.0%, or 0.025% to 0.075%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference in their entirety, unless explicitly indicated otherwise. The present disclosure shall control in the event there are any disparities between any definitions and/or description found in the cited references.

Unless otherwise specified or indicated by context, the terms "a", "an", and "the" mean "one or more." For example, "a protein" or "an RNA" should be interpreted to mean "one or more proteins" or "one or more RNAs," respectively.

The Examples provided below are meant to be illustrative and not to limit the scope of the invention or the claims. All references and appendices cited herein are hereby incorporated by reference in their entireties.

EXAMPLES

Example 1. Mutation of RGD Motif in SVNV Inhibits Transmission of Orthotospoviruses The RGD motif is present in glycoprotein N of SVNV and several other orthotospoviruses belonging to the American clade of the genus (Chen et al., 2013). Its function in virus attachment/entry to thrips midgut cells and the potential effect of this interaction on transmission of orthotospoviruses, however, is not well-understood. We hypothesize that the RGD motif as well as the N-linked glycosylation site of the SVNV $G_N$ protein ($N_{229}$ based on in-silico simulations) are critical in the early steps of virus infection process, and will decrease transmission efficiency when receptors are saturated with ligands prior to acquisition. To test this hypothesis, we developed peptides with single, double and triple amino acids mutations at the $RGD_{29-31}$ site and $N_{229}$ using alanine scanning and evaluated their effect on transmission.

Materials and Methods

*Neohydatothrips variabilis* Rearing

*Neohydatothrips variabilis* adults were collected from soybean fields and placed on leaf discs, floating on water, for 10-15 days to allow for oviposit. Hatched larvae were transferred to leaf discs and reared to adults. They were collected and released to soybean seedlings maintained under controlled environment (27° C., 16 h photoperiod); with seedlings renewed biweekly. Plants were tested using ELISA and/or RT-PCR for SVNV as described previously (Zhou and Tzanetakis, 2013; Zhou et al, 2018).

Peptides Design and Synthesis

In-silico analysis of the SVNV $G_N$ protein using MatGAT, TMHMM2.0 and NetNGlyc1.0 revealed the presence of signature motifs present in orthotospovirus orthologs including a $RGD_{29-31}$ domain, several putative N-linked glycosylation sites ($N_{25, 229, 343}$) and transmembrane domains ($aa_{6-28, 317-339, 349-371}$) (Krogh et al., 2001; Campanella et al; 2003; Julenius et al., 2005; Zhou et al., 2011) (FIG. 1). The two putative glycosylated residues located within or in close proximity to transmembrane domains ($Asn_{25}$ and $Asn_{343}$) were not included in downstream experiments as they are probably unavailable for binding based on the in-silico analysis. Polypeptides were designed around the $RGD_{29-31}$ domain and $Asn_{229}$; and two sequences were selected for synthesis based on the predicted solubility: NASIRGDHEVSQE$_{25-37}$ (SEQ ID NO. 1) and RLTGECNITKVSLTN$_{215-229}$ (SEQ ID NO. 2). Peptides with single, double or triple mutations at $RDG_{29-31}$ and $N_{229}$ are described in Table 1. All peptides were synthesized at GenScript (NJ, U.S.; >95% purity).

Peptide Delivery

Peptides RGD, AGD, RGA, AGA, RAA, AAA and $N_{229}$ were dissolved in molecular biology grade water; peptides RAD and AAD were dissolved in water containing 28-30% $NH_4OH$ as they were insoluble in $H_2O$; $A_{229}$ did not dissolve in either water or 25% acetic acid (as suggested by the manufacturer).

The peptide solution was diluted to 10 nM using feeding buffer (8% sucrose, 20% blue food dye). Peptides were pipetted onto an Eppendorf tube lid and sealed with a piece of stretched parafilm. First instar larvae, hatched within 24 h of the initiation of the feeding experiments were collected from SVNV-free leaf discs and individually transferred to the bottom of the tube. Tubes were placed in a black-colored microtube rack under a light source to attract larvae to move upward and feed on the peptide solution. The potential effect of the peptides on transmission efficiency, was studied using the treatments listed in Table 2.

First instar larvae were fed on peptide solution for 5 h and transferred onto SVNV-infected soybean leaf tissue for virus acquisition. Soybean leaflets showing typical SVNV symptoms (vein-clearing and chlorosis) and tested positive for SVNV by RT-PCR were used as virus source. After a 16 h acquisition access period (AAP), larvae were transferred to a SVNV-free leaf disc. Larvae were reared until the $2^{nd}$ larval stage. Control groups included a) larvae fed on feeding buffer and b) larvae fed on feeding buffer before exposed to the virus. The transmission baseline was established by feeding larvae only on infected tissue.

Peptide Effects on Transmission

Single second instar larvae were transferred to the leaf blade of a soybean seedling at unifoliate stage. To prevent larval escape, pots were covered with a thrips-proof cage. The caged seedlings were grown at 27° C., 16 h photoperiod. Thrips were allowed to feed, develop to adults and propagate; 20 d post transfer, cages were removed and plants were screened for SVNV infection using dot-blot immunoassay and RT-PCR as previously described (Zhou and Tzanetakis, 2013; Zhou et al, 2018). The data was analyzed using one-way analysis of variance (ANOVA) on percentage of virus infection and percentage of thrips feeding using JMP Pro 13 (SAS Institute Inc., Cary, NC) and Dunnett's test (Dunnett, 1955) was used in the post hoc test.

Peptide Sequencing

To further confirm the sequences of the RGD and AAA peptides, they were analyzed using MALDI-TOF-MS and LC-ESI-MS/MS at the Mass Spectrometry Facility Center of University of Arkansas (Fayetteville, U.S.) as previously described (Caprioli et al., 1997; Dams, et al., 2003).

Analysis of peptides RDG and AAA using MALDI-TOF-MS revealed single peaks at 1441.9 KD and 1326.6 KD, respectively (FIG. 8A). These values corresponded to their individual molecular mass provided by GenScript (NJ, USA) indicating their intact masses. Notwithstanding and in order to confirm results beyond doubt, their sequences were further confirmed by LC-ESI-MS/MS (FIGS. 8B and 8C).

Results

Polypeptide Design and Delivery

Polypeptides were designed around the $RGD_{29-31}$ domain and $Asn_{229}$; and two sequences were selected for synthesis based on the predicted solubility: NASIRGDHEVSQE$_{25-37}$ (SEQ ID NO. 1) and RLTGECNITKVSLTN$_{215-229}$ (SEQ ID NO. 2). Peptides with single, double or triple mutations at $RDG_{29-31}$ and $N_{229}$ are described in Table 1; mutated amino acids are highlighted in bold. All peptides were synthesized at GenScript (NJ, U.S.; >95% purity).

A homogeneous blue color observed through the abdomen of the larvae after feeding with peptide solution was used as an indicator of successful peptide delivery (FIG. 2) and only blue larvae were harvested and used for downstream experiments.

Transmission

Four feeding groups (peptide/SVNV, buffer/SVNV, buffer, SVNV) including nine treatments (Table 2) were analyzed for thrips ability to transmit the virus. Dot blot results showed a perfect correlation between typical SVNV symptoms and local lesions on leaf surface (Zhou and Tzanetakis, 2013). For plants that only exhibit local lesions, RT-PCR was used to detect the presence of SVNV given that the amount of symptomatic leaf tissue was not enough for dot blot detection (Zhou and Tzanetakis, 2013). Stippling, scars and distorted appearances on plant surface verified thrips feeding. Plants lacking such signs were excluded from the analysis. Each treatment was repeated in three experiments with multiple thrips tested. The ratio of number of plants fed by thrips to total number of plants transferred with thrips and the ratio of number of plants infected with SVNV to number of plants fed by thrips were calculated for each replicate, respectively, together with their percentages (Table 2). In addition, to serve as the technical control of the experiment, SVNV treatment (where thrips were exposed to the virus) also revealed the transmission efficiency of single thrips.

Figure 3:
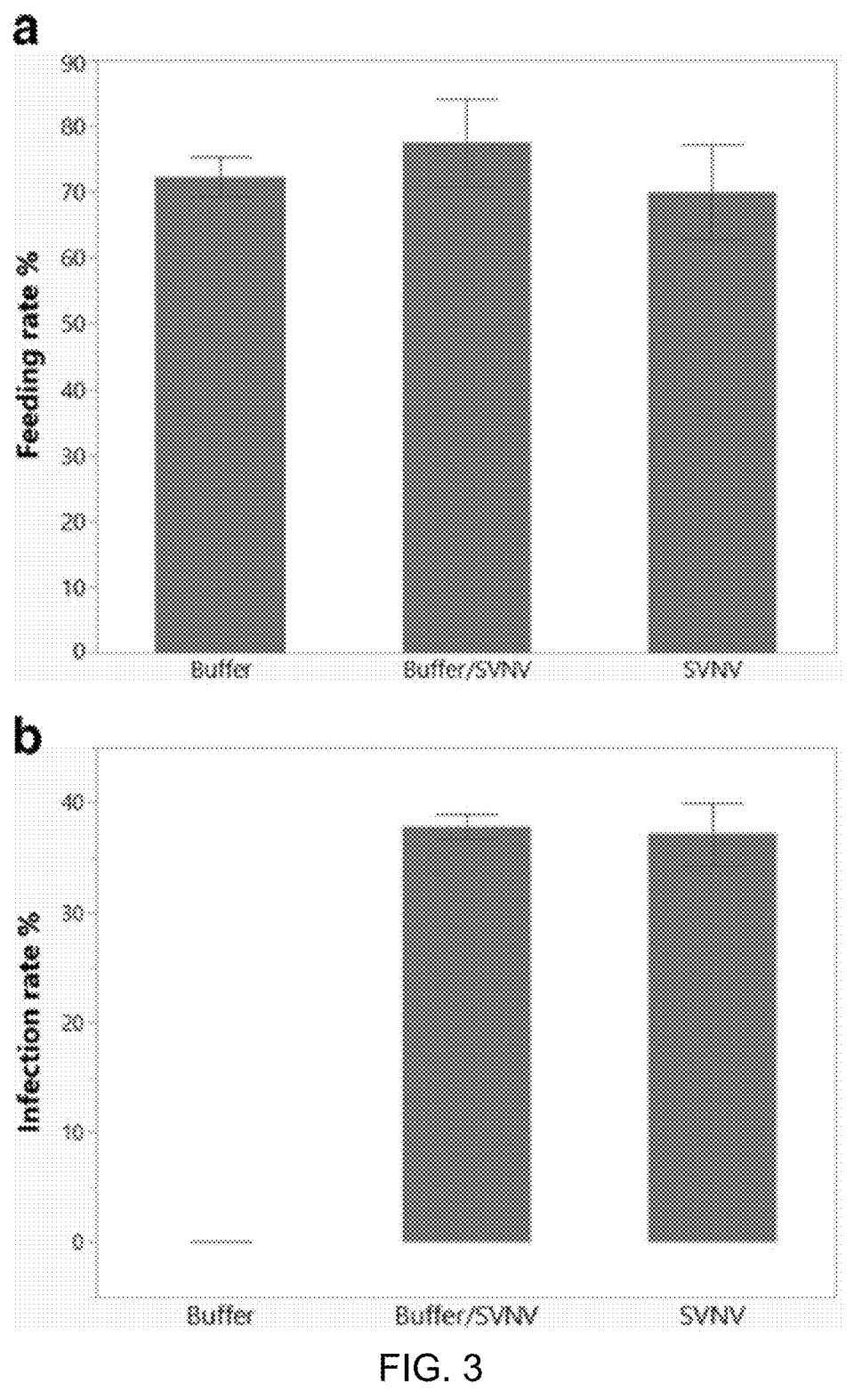
Figure 6:
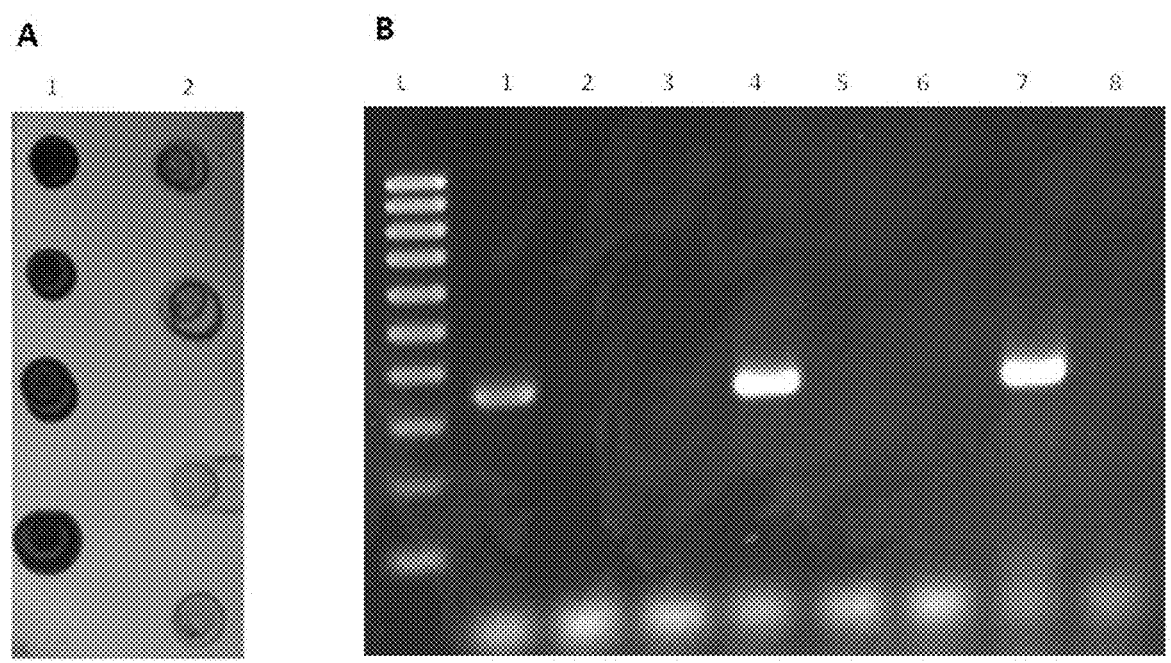
FIG. 6 shows a dot-blot immunoassay and RT-PCR detection of SVNV. (A) is a dot-blot assay. Lane 1: SVNV-positive and; lane 2: SVNV-negative. (B) RT-PCR detection of SVNV. L: DNA ladder; Lanes 1, 4, and 7: SVNV-positive samples with amplicon size of 348 bp; Lanes 2, 3, 5, 6, and 8: SVNV-negative samples.
Figure 7:
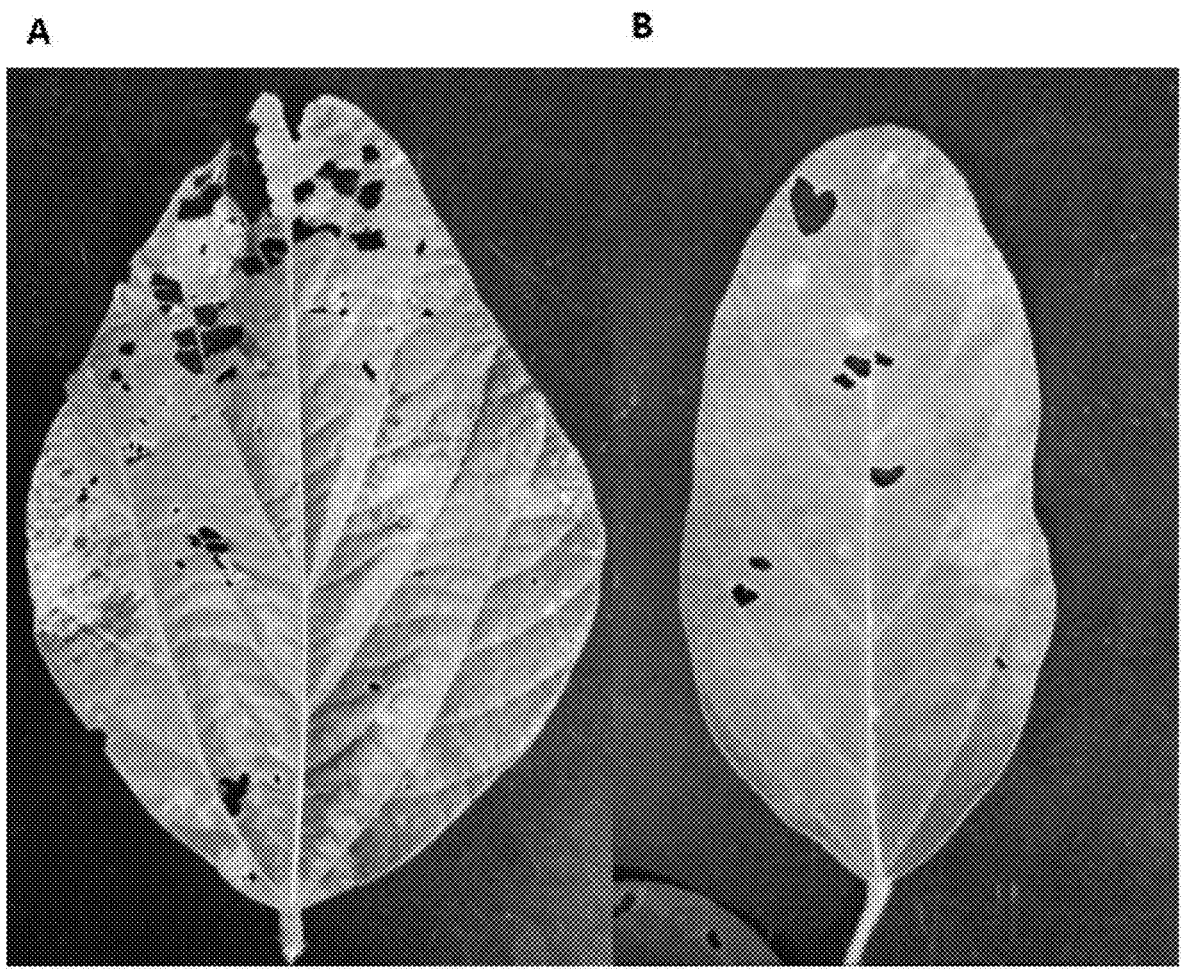
FIG. 7 demonstrates the typical SVNV symptoms of a leaf. (A) demonstrates vein chlorosis and (B) vein clearing.

Dot-blot and RT-PCR results were in concordance with typical SVNV symptoms and local lesions on the leaf surface FIG. 6 and FIG. 7. Virus infection rate and thrips' feeding rate were calculated for individual treatment (Table 2). The comparison of thrips' feeding rate among treatments fed with buffer/SVNV, buffer and SVNV indicates feeding buffer does not have an impact on the fitness of individuals (P>0.05; FIG. 3a). In addition to serve as the technical control of the experiment, treatment SVNV (where thrips were exposed to the virus alone) also revealed the transmission efficiency of individual thrips (Table 2).

Figure 4:
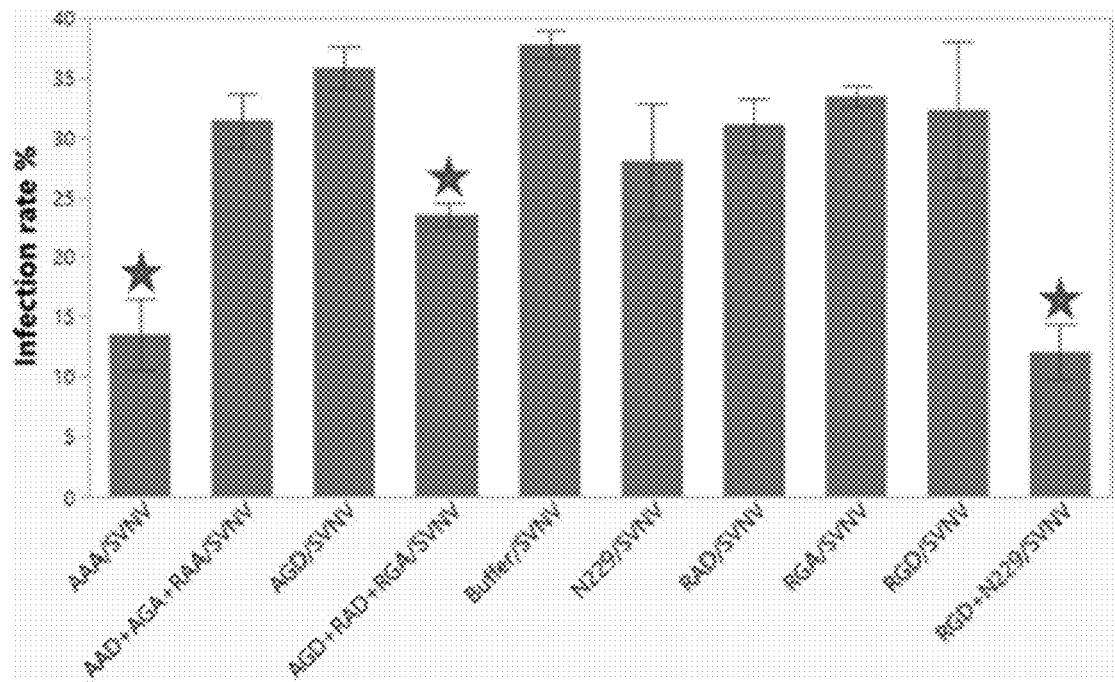
FIG. 4 shows SVNV infection rate of different treatments with different polypeptides.
Figure 5:
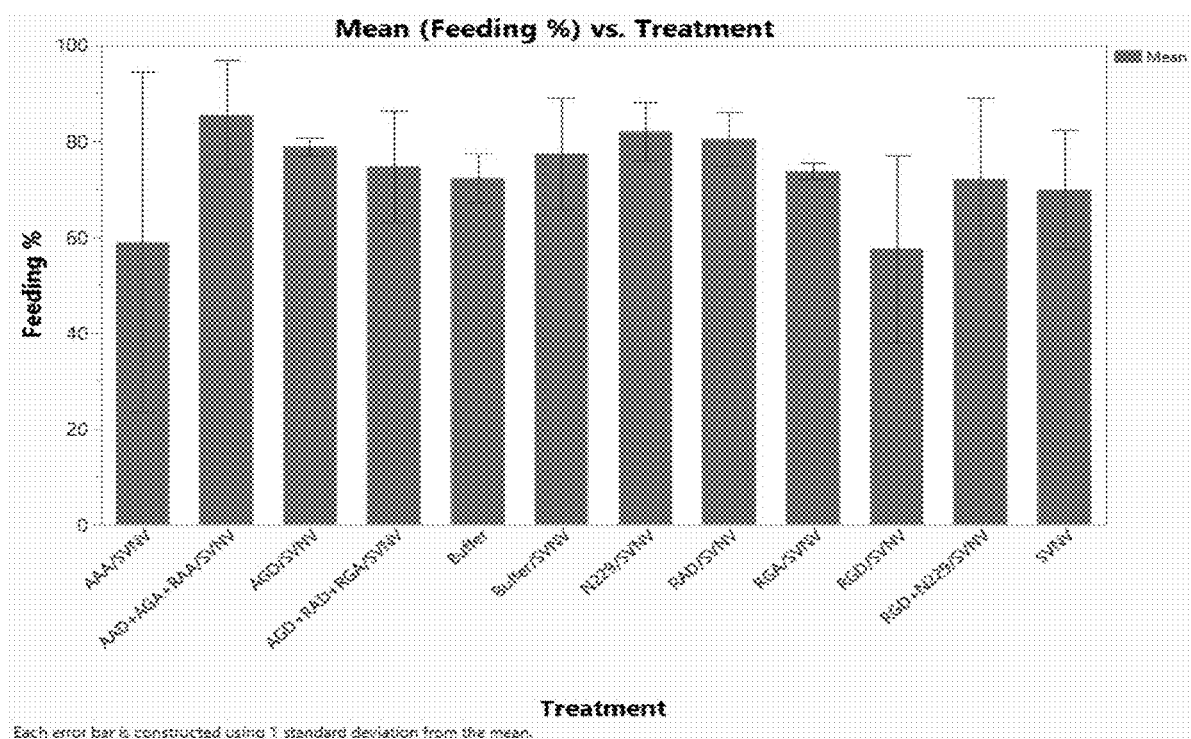
FIG. 5 shows thrips feeding rate of different treatments with different polypeptides.

SVNV infection and thrips' feeding rates were analyzed using one-way ANOVA. Analysis of infection rate revealed a significant difference between treatments (P<0.0001; FIG. 5). The post hoc test using Dunnett's method suggested that treatments fed with wild-type peptides (RGD+N229), single-mutation peptides' combination (AGD+RAD+RGA) and triple-mutation peptide (AAA) had significantly lower infection rates (P<0.05) with 68.3, 37.4 and 68.3% reduction, respectively when compared with the control group (thrips fed on feeding buffer prior to the virus exposure). Whereas treatments in which the thrips were fed with a combination of double-mutation peptides (AAD+AGA+RAA), RGD29-31 or N229, respectively did not have significant difference (P>0.05); only 17.8, 0 and 25.9% reductions were observed, respectively. In addition, the infection rate of the control group did not differ significantly from the group fed on SVNV-infected tissue (FIG. 3b). In terms of feeding rate, the analysis did not reveal a significant difference among different treatments (P>0.05; FIG. 4); neither did the significant linear relationship exist between feeding and infection rates (P=0.3828).

TABLE 2

Transmission inhibition assays.

| Treatment | Experiment 1 Feeding | Experiment 1 Infection | Experiment 2 Feeding | Experiment 2 Infection | Experiment 3 Feeding | Experiment 3 Infection | Total Feeding | Total Infection |
|---|---|---|---|---|---|---|---|---|
| RGD + $N_{229}$/SVNV | 60/88 (68.2%) | 10/60 (16.7%) | 69/76 (90.8%) | 7/69 (10.1%) | 53/92 (57.6%) | 5/53 (9.4%) | 182/256 (71.1%) | 22/182 (12.1%) |
| AGD + RAD + RGA/SVNV | 53/80 (66.3%) | 13/53 (24.5%) | 42/60 (70.0%) | 9/42 (21.4%) | 89/101 (88.1%) | 22/89 (24.7%) | 184/241 (76.3%) | 44/184 (23.9%) |
| AAD + AGA + RAA/SVNV | 73/100 (73%) | 23/73 (31.5%) | 71/80 (88.8%) | 25/71 (35.2%) | 76/80 (95%) | 21/76 (27.6%) | 220/260 (84.6%) | 69/220 (31.4%) |
| AAA/SVNV | 26/100 (26%) | 5/26 (19.2%) | 65/120 (54.2%) | 6/65 (9.2%) | 58/60 (96.7%) | 7/58 (12.1%) | 149/280 (53.2%) | 18/149 (12.1%) |
| AGD/SVNV | 48/60 (80%) | 16/48 (33.3%) | 28/35 (80%) | 11/28 (39.3%) | 43/56 (76.8%) | 15/43 (34.9%) | 119/151 (78.8%) | 42/119 (35.3%) |
| RAD/SVNV | 52/60 (86.7%) | 14/52 (26.9%) | 26/33 (78.8%) | 9/26 (34.6%) | 41/54 (75.9%) | 13/41 (31.7%) | 119/147 (81%) | 36/119 (30.3%) |
| RGA/SVNV | 44/60 (73.3%) | 15/44 (34.1%) | 41/54 (75.9%) | 13/41 (31.7%) | 29/40 (72.5%) | 10/29 (34.5%) | 114/154 (74%) | 38/114 (33.3%) |
| RGD/SVNV | 17/45 (37.8%) | 4/17 (23.5%) | 23/30 (76.7%) | 7/23 (30.4%) | 93/160 (58.1%) | 40/93 (43.0%) | 133/235 (56.6%) | 51/133 (38.3%) |
| $N_{229}$/SVNV | 37/44 (84.1%) | 7/37 (18.9%) | 20/23 (87.0%) | 7/20 (35%) | 116/154 (75.3%) | 35/116 (30.2%) | 173/231 (74.9%) | 49/173 (28.3%) |
| Buffer/SVNV | 38/56 (67.9%) | 14/38 (36.8%) | 63/85 (74.1%) | 23/63 (36.5%) | 95/105 (90.5%) | 38/95 (40.0%) | 196/246 (79.6%) | 75/196 (38.2%) |
| SVNV | 35/46 (76.1%) | 13/35 (37.1%) | 43/55 (78.2%) | 18/43 (41.9%) | 74/133 (55.6%) | 24/74 (32.4%) | 152/234 (65.0%) | 55/152 (36.2%) |
| Buffer | 42/63 (66.7%) | 0/42 (0%) | 68/93 (73.1%) | 0/68 (0%) | 54/70 (77.1%) | 0/54 (0%) | 164/226 (72.6%) | 0/164 (0%) |

In Table 2, Feeding refers to number of plants with feeding scars/plants exposed to thrips; Infection refers to number of SVNV-infected plants/plants with feeding scars. The numbers in parenthesis indicate the percentile of feeding and infection for each treatment.

Statistical Analysis

SVNV infection (FIG. 4) and thrips feeding rates (FIG. 5) were analyzed using One-way ANOVA. Analysis of infection rate reveals a significant difference between treatments (P<0.0001). The post hoc test using Dunnett's method suggests that treatments fed with wild-type peptides (RGD+$N_{229}$), single-mutation peptides combination (AGD+RAD+RGA) and triple-mutation peptide (AAA) have significantly lower infection rates (P<0.05) with 68.3%, 37.4% and 68.3% reduction, respectively, when compared with the control group (thrips fed on feeding solution prior to the virus exposure). Whereas treatments fed with double-mutation peptides combination (AAD+AGA+RAA), $RGD_{29-31}$ or $N_{229}$ did not have pronounced difference (P>0.05); only 17.8%, 0% and 25.9% reduction were observed respectively. In addition, the infection rate of control group does not differ significantly from the group fed on SVNV-infected tissue (Table 3). In terms of feeding rate, the analysis did not reveal a significant difference among treatments (P>0.05; FIG. 5 and Table 4); there is not a significant linear relationship between feeding and infection rates (P=0.3828) either.

TABLE 3

Comparison of infection rates (mean ± standard error) among treatments.

| Treatment | P-value | Infection rate (mean ± standard deviation) |
|---|---|---|
| RGD + $N_{229}$/SVNV | <0.0001 | 12.07 ± 4.03 |
| AGD + RAD + RGA/SVNV | 0.02 | 23.53 ± 1.85 |
| AAD + AGA + RAA/SVNV | 0.58 | 31.43 ± 3.80 |
| AAA/SVNV | <0.0001 | 13.50 ± 5.14 |
| AGD/SVNV | 1.00 | 35.83 ± 3.11 |
| RAD/SVNV | 0.50 | 31.07 ± 3.89 |
| RGA/SVNV | 0.89 | 33.43 ± 1.51 |
| RGD/SVNV | 0.71 | 32.30 ± 9.89 |
| $N_{229}$/SVNV | 0.14 | 28.03 ± 8.27 |
| Buffer/SVNV (Control) | 1.00 | 37.77 ± 1.94 |
| SVNV | 1.00 | 37.13 ± 4.75 |
| Buffer | <0.0001 | 0 |

TABLE 4

Comparison of feeding rates (mean ± standard error) among treatments.

| Treatment | P-value | Feeding rate (mean ± standard deviation) |
|---|---|---|
| RGD + $N_{229}$/SVNV | 1.00 | 72.20 ± 16.96 |
| AGD + RAD + RGA/SVNV | 1.00 | 74.80 ± 11.67 |
| AAD + AGA + RAA/SVNV | 0.99 | 85.60 ± 11.34 |
| AAA/SVNV | 0.66 | 58.97 ± 35.59 |
| AGD/SVNV | 1.00 | 78.93 ± 1.85 |
| RAD/SVNV | 1.00 | 80.47 ± 5.59 |
| RGA/SVNV | 1.00 | 73.9 ± 1.78 |
| RGD/SVNV | 0.59 | 57.53 ± 19.46 |
| $N_{229}$/SVNV | 1.00 | 82.13 ± 6.09 |
| Buffer/SVNV | 1.00 | 77.50 ± 11.68 |
| SVNV | 0.99 | 69.97 ± 7.21 |
| Buffer | 1.00 | 72.30 ± 5.25 |

Peptide Sequencing

Analysis of peptides RDG and AAA using MALDI-TOF-MS revealed single peaks at 1441.9 KD and 1326.6 KD, respectively. These values correspond to their individual molecular mass provided by GenScript (NJ, U. S.) indicating their intact masses. Moreover, their sequences were further analyzed by LC-ESI-MS/MS; results showed expected sequences as designed.

DISCUSSION

In the presence of RGD and $Asn_{229}$ peptides, transmission was greatly reduced (P<0.0001). When thrips were fed with either peptide separately there was no significant reduction in transmission compared to control (RGD: P=0.72; $Asn_{229}$: P=0.18). These results indicate that both the RGD and $Asn_{229}$ motifs are needed for successful cell entry and therefore transmission. To test this hypothesis, we synthesized a peptide where $Asn_{229}$ was substituted by Ala. The insolubility of this peptide, however, prevented further evaluation of the role of $Asn_{229}$ in virus transmission.

Evaluating the transmission rate of larvae fed with a combination of peptides consisting of different mutated RGD sequences is the preliminary step to identify peptide(s) with key amino acid(s) in virus transmission. Some peptides lost their binding activity to receptors due to the key amino acids for such activity was substituted with Ala, whereas some still retained this function because Ala replaced non-essential amino acids. Peptides combination consist of single-amino acid mutations including AGD, RAD and RGA exhibit inhibitory effect on virus transmission when compared with control group (Table 3). However, such inhibitory effects are less potent than the group fed with peptides containing $RGD_{29-31}$ and $Asn_{229}$ (Table 3). A possible explanation is that single-amino acid mutants bind with cellular receptors but with either weaker strength or coverage, which lead to partial blockage of the receptors. Such suppression on virus transmission was further diminished by replacing two amino acids with Ala residues: the transmission rate of double-mutants group containing sequences of AAD, AGA and RAA is not significantly lower than the control groups (Table 3). These results follow the line of logic that RGD motif is essential in virion-cell attachment and the disruption of this region impairs vector acquisition.

The contribution of individual amino acids consisting RGD motif in virus transmissibility seems to vary among different pathosystems, and the amino acid residue utilized to generate mutants may affect the results of mutagenesis studies. In adenovirus type 2 where $RGD_{340-342}$ of the penton base protein, substitution of Arg340Ser, Gly341Val and Asp342Glu abolished virus activity respectively suggesting each amino acid is crucial for the infection process (Bai, et al., 1993). On the other hand, Wei et al. (2014) found Arg and Gly but not the Asp were essential for fusion activity for Human metapneunovirus. In the case of foot-and-mouth disease virus (FMDV), its virulence is abolished by replacing Asp143Ala of the $RGD_{141-143}$ motif but not by mutants targeting the other two residues (Gutiérrez-Rivas et al., 2008). To role of individual amino acids consisting RGD motif in the transmission of SVNV was evaluated as well. Compared to control group, thrips fed with peptides AGD, RAD and RGA, respectively prior to virus acquisition, did not exhibit significant lower levels on virus infection rate (Table 3), suggesting neither residue tested here functions as the key element for virus transmission by its own.

Figure 8:
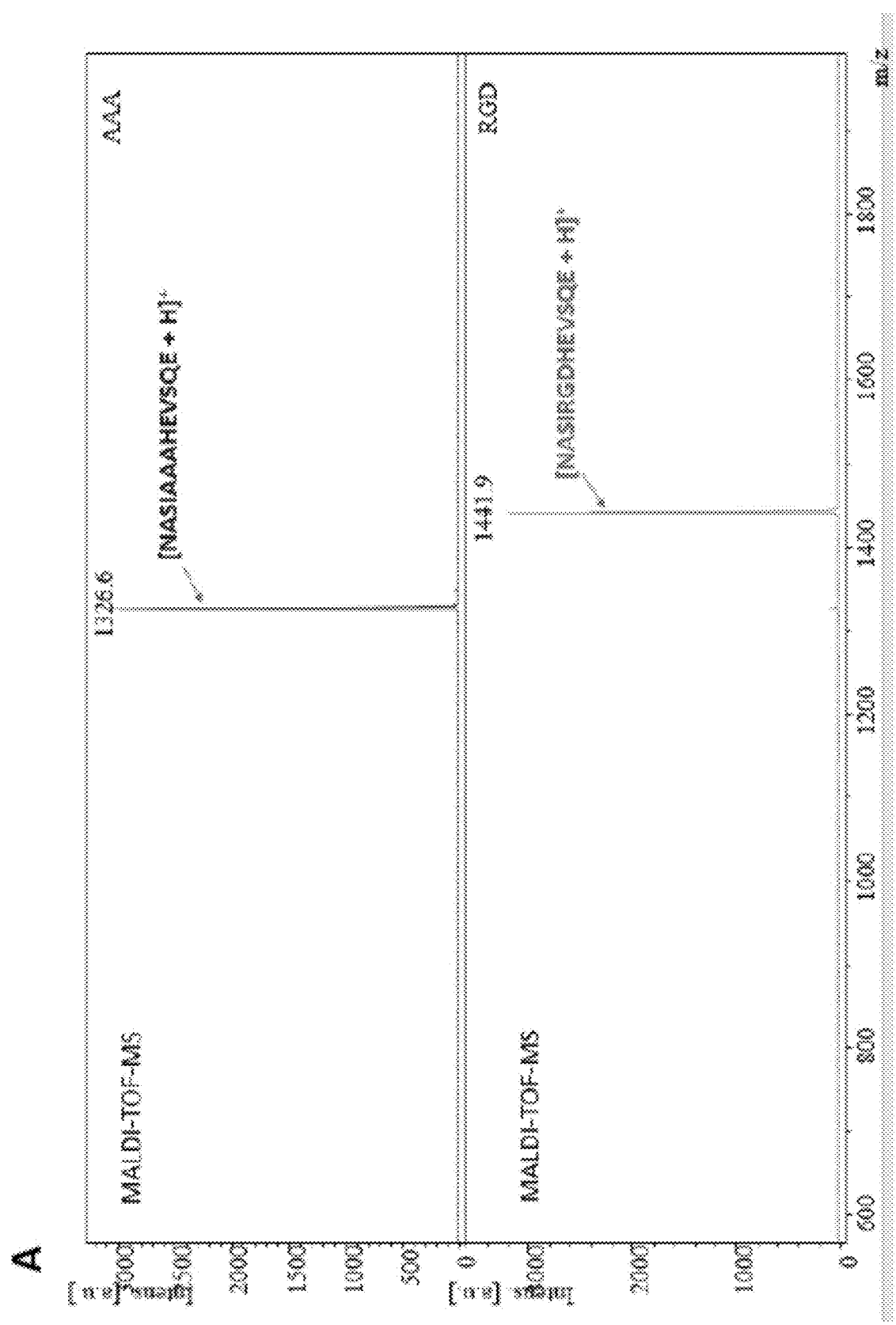
FIG. 8 shows the analysis of molecular masses and amino acid sequences of peptides RGD and AAA. (A) analysis of molecular masses using MALDI-TOF-MS; (B) analysis of sequences using LC-ESI-MS/MS for RGD; (C) analysis of sequences using LC-ESI-MS/MS for AAA.
Figure 8:
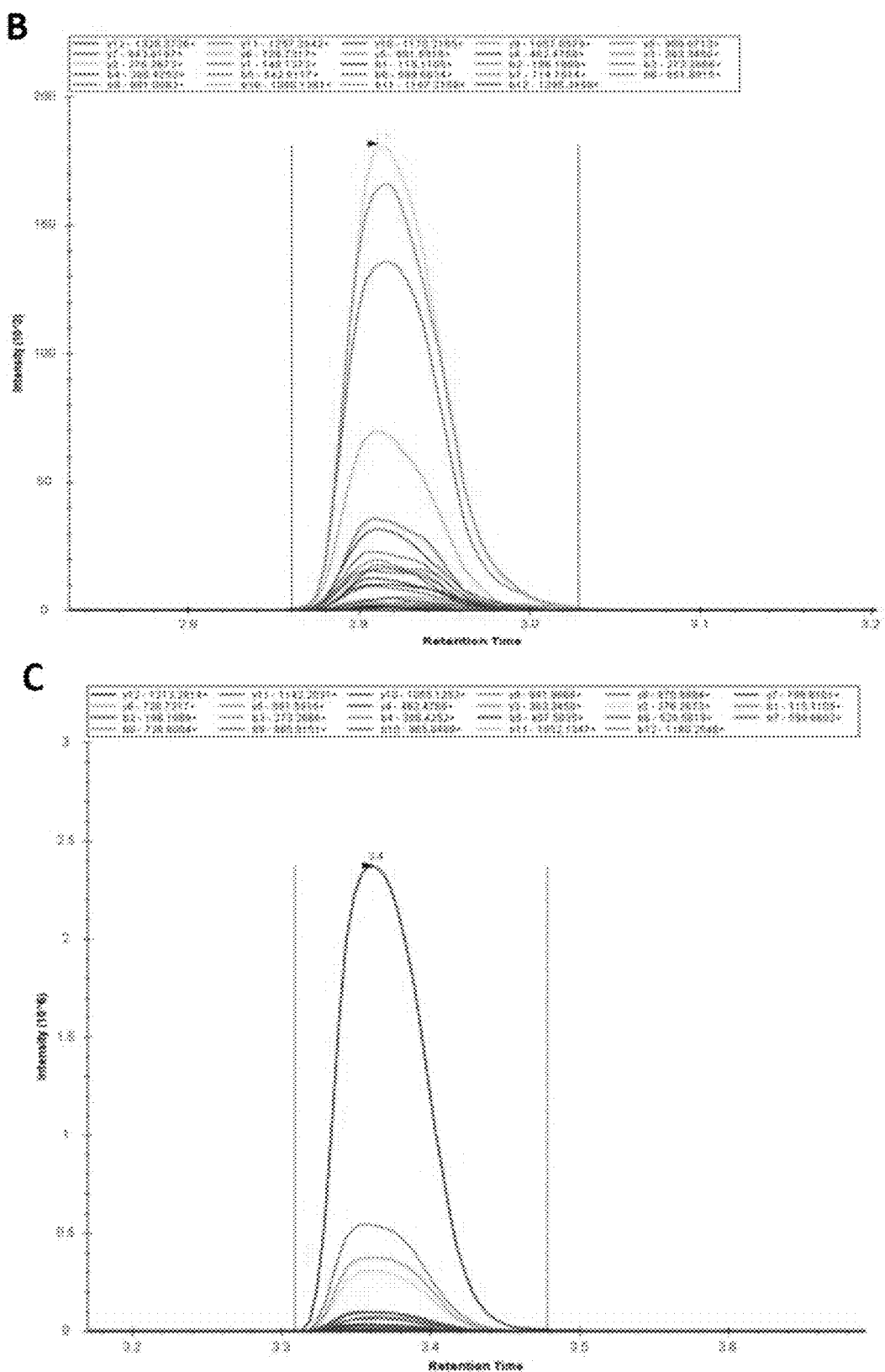

Two peptide treatments produced intriguing results and for this reason the molecular masses and amino acid sequences of RGD and AAA were confirmed by MALDI-TOF-MS and LC-MS/MS to exclude the possibility of mislabeling (FIG. 8). The transmission rate of RGD is not significantly lower than the controls and unlike $RGD/Asn_{229}$ (Table 3), indicating that probably both $RGD_{29-31}/Asn_{229}$ motifs are needed for efficient virus entry, which corroborates the results obtained from AGD, RAD and RGA individual feeding groups. The transmission rate of AAA is comparable to that of $RGD/Asn_{229}$ (Table 3). It is possible that the triple mutant blocks the cellular receptor, leading to transmission suppression. By reducing the load of virus particles on epithelium cells, the transmission efficiency diminishes. This hypothesis is supported by the fact that the myristoylated alanine-rich C-kinase substrate (MARCKS) protein inhibits cellular adhesion to extracellular matrix proteins including fibronectin (Spizz and Blackshear, 2001), a phenomenon that could also occur in the presence the RGD motif, which is a known fibronectin competitive inhibitor (Pierschbacher and Ruoslahti, 1984). Alanine-rich protein/peptides could inhibit cellular binding not only to endogenous integrin-binding proteins that contain the RGD motif but also RGD-containing viral proteins, such as the SVNV $G_N$ protein, leading to the reduction of virus transmission. Moreover, given the fact that MARCKS inhibition of cell adhesion is independent of direct integrin receptor modulation (Spizz and Blackshear, 2001), alanine-rich proteins/peptides may be promising in impeding virus entry regardless of the type of host cellular receptors.

The observed results could also be due to in vivo factors that influence the binding of the RGD motif. The microenvironment of virion-cell attachment consists of several components including 1) host cells with integrin incorporated on their surface, 2) viruses which recognize cells through the integrin-binding domains of the virus glycoproteins and 3) native integrin-binding proteins which do not exist in in vitro experiments and may have not been identified in in vivo studies. The endogenous integrin-binding proteins known as fibronectin, fibrinogen and vitronectin and other glycoproteins are present in blood and other body fluids of vertebrates at high concentrations (Bellis, 2011; Schwab et al., 2013). Despite of the lack of information on their presence in thrips, as the essential players of the evolutionary conserved cell-adhesion systems, these integrin receptors have also been identified in different species of invertebrates including arthropods (Akiyama and Johnson, 1983; Pradel et al., 2004; Hanington and Zhang, 2010). The binding signal triggered by these proteins to integrins on host cell surface is more robust than exogenous factors (Woods et al., 1986; Aota et al., 1991). The addition of the triple mutant peptide may have stimulated the secretion of endogenous integrin-binding proteins through interacting with proteins involved in related molecular pathways, similar to peptides interfering with protein-protein interaction in the ethylene signaling pathway (Bisson et al., 2016), causing saturation of integrin-binding sites and consequently blocking the attachment of virions to host cells.

On the other hand, the results obtained from RGD and AAA may indicate that the interaction between SVNV and *N. variabilis* could also involve non-RDG components. This hypothesis is supported by the fact that among all-characterized orthotospoviruses, only members belonging to American clade contain RGD motifs in their respective $G_N$ proteins (Chen et al., 2013). Molecular signals mediating cell-virion attachment in Euroasian clade have not been identified to date. These viruses utilize RGD-independent mechanisms such as lectin-like domain identified in TSWV $G_N$ protein to get access to host cells (Whitfield, 2004).

Independent of the mechanism behind the inhibitory action of the studied peptides, it is clear that they affect virus transmission. Whether the reduction in transmission efficiency is due to peptide-blockage of cellular receptor needs to be elucidated. Although the amino acid composition of RGD is crucial in integrin-mediated cell attachment, it is also essential that viral glycoprotein correctly folded so the motif is exposed at the surface of the protein, making it accessible to its receptors. On the other hand, the stereochemistry of RGD peptide also influences the interaction between integrin receptors and the motif. Amino acid substitution in the flanking sequences could alter binding specificity and strength of the conserved motif to its receptors (Pierschbacher and Ruoslahti, 1987; Plow et al., 1987; Liu et al., 1994; Haubner et al., 1996). Likewise, three-dimensional peptide conformations have similar effects; for example the linear RGD sequences such as GRGDSP (SEQ ID NO: 11) and RGDSPASSKP (SEQ ID NO: 12) bind preferentially to α5β1, whereas their cyclic counterparts GPenGRGDSPCA (SEQ ID NO: 13) and cyclo (RGDf (NMe)V) (SEQ ID NO: 14) are selective for αvβ3 (Hersel et al., 2003). Additionally, it is also important RGD sequence is presented in a context that can be recognized by integrin and compatible with its binding (Bellis, 2011).

CONCLUSION

The transmission efficiency of SVNV by individual *N. variabilis* is over 36%, underlining the importance of disrupting virus-thrips interaction for effective virus control. The analysis of transmission efficiency mediated by synthetic polypeptides revealed that peptides derived from $RGD_{29-31}$ and $N_{229}$ motifs located at viral glycoprotein had the potential of blocking virion attachment to cellular receptors and consequently decreasing virus transmission efficiency.

REFERENCES

Akiyama, S. K. and Johnson, M. D. 1983. Fibronectin in evolution: presence in invertebrates and isolation from Microciona prolifera. Comparative Biochemistry and Physiology. B. 76:687-694.

Aota, S., Nagai, T. and Yamada, K. M. 1991. Characterization of regions of fibronectin besides the arginine-glycine-aspartic acid sequence required for adhesive function of the cell-binding domain using site-directed mutagenesis. The Journal Biological Chemistry. 266: 15938e43.

Arosio, D., Casagrande, C. and Manzoni, L. 2012. Integrin-mediated drug delivery in cancer and cardiovascular diseases with peptide-functionalized nanoparticles. Current Medicinal Chemistry. 19:3128-3151.

Badillo-Vargas, I. E. 2014. Dissecting the molecular interplay between Tomato spotted wilt virus and the insect vector, *Frankliniella occidentalis*. Kansas State University, Manhattan, U. S.

Bai, M., Harfe, B. and Freimuth, P. 1993. Mutations the alter the Arg-Gly-Asp (RGD) sequence in the adenovirus type 2 penton base protein abolish its cell-rounding activity and delay virus reproduction in flat cells. Journal of Virology. 67:5198-5205.

Bellis, S. L. 2011. Advantages of RGD peptides for direction cell association with biomaterials. Biomaterials. 32:4205-4210.

Bisson, M. M., Kessenbrock, M., Müller, L., Hofmann, A., Schmitz, F., Cristescu, S. M. and Groth, G. Peptides interfering with protein-protein interactions in the ethylene signaling pathway delay tomato fruit ripening. Scientific Reports. 6:30634.

Borrego, P., Calado, R., Marcelino, J. M., Pereira, P., Quintas, A., Barroso, H. and Taveira, N. 2013. An ancestral HIV-2/simian immunodeficiency virus peptide with potent HIV-1 and HIV-2 fusion inhibitor activity. AIDS. 27:1081-1090.

Campanella, J. J., Bitincka, L. and Smalley, J. 2003. MatGAT: an application that generates similarity/identity matrices using protein or DNA sequences. BMC Bioinformatics. 4:1-4.

Caprioli, R. M., Farmer, T. B. and Gile, J. 1997. Molecular imaging of biological samples: localization of peptides and proteins using MALDI-TOF MS. Analytical Chemistry. 69:4751-4760.

Chen, T. C., Li, J. T., Fan, Y. S., Yeh Y. C., Yeh, S. D. and Kormelink, R. 2013 Molecular characterization of the full-length L and M RNAs of Tomato yellow ring virus, a member of the genus Tospovirus. Virus Genes. 46:487-495.

Dams, R., Huestis, M. A., Lambert, W. E. and Murphy, C. M. 2003. Matrix effect in bio-analysis of illicit drugs with LC-MS/MS: influence of ionization type, sample preparation, and biofluid. Journal of the American Society for Mass Spectrometry. 14:1290-1294.

Dunnett, C. W. 1955. A multiple comparison procedure for comparing several treatments with a control. Journal of the American Statistical Association. 50:1096-1121.

Firbas, C., Jilma, B., Tauber, E., Buerger, V., Jelovcan, S., Lingnau, K., Buschle, M., Frisch, J. and Klade, C. S. 2006. Immunogenicity and safety of a novel therapeutic hepatitis C virus (HCV) peptide vaccine: a randomized, placebo controlled trial for dose optimization in 128 healthy subjects. Vaccine. 24:4343-4353.

Gosselet, F., Saint-Pol, J., Candela, P and Fenart, L. 2013. Amyloid-beta peptides, Alzheimer's disease and the bold-brain barrier. Current Alzheimer Research. 10:1015-1033.

Gutiérrez-Rivas, M., Pulido, M. R., Baranowski, E., Sobrino, F. and Sáiz, M. Tolerance to mutations in the foot-and mouth disease virus integrin-binding RGD region is different in cultured cells and in vivo and depends on the capsid sequence context. Journal of General Virology. 89:2531-2539.

Hanington, P. C. and Zhang, S-M. 2010. The primary role of fibrinogen-related proteins in invertebrates is defense, not coagulation. Journal of Innate Immunity. 3:17-27.

Haubner, R., Gratias, R., Diefenbach, B., Goodman, S. L., Jonczyk, A. and Kessler, H. 1996. Structural and functional aspects of RGD-containing cyclic pentapeptides as highly potent and selective integrin alphavbeta3 antagonists. Journal of the American Chemical Society. 118:7461-7472.

Hersel, U., Dahmen, C. and Kessler, H. 2003. RGD modified polymers: biomaterials for stimulated cell adhesion and beyond. Biomaterials. 24:4385-4415.

Hipolito, S. G., Shitara, A., Kondo, H. and Hirono, I. 2014. Role of Marsupenaeus japonicas crustin-like peptide against Vibrio penaeicida and white spot syndrome virus infection. Developmental and Comparative Immunology. 46:461-469.

Houimel, M. and Dellagi, K. 2009. Peptide mimotopes of rabies virus glycoprotein with immunogenic activity. Vaccine. 27:4648-4655.

Julenius, K., MØlgaard, A., Gupta, R. and Brunak, S. 2005. Prediction, conservation analysis, and structural characterization of mammalian mucin-type O-glycosylation sites. Glycobiology. 15:153-164.

Krogh, A., Larsson, B., von Heijne, G. and Sonnhammer, E. L. 2001. Predicting transmembrane protein topology with a hidden Markov model: application to complete genomes. Journal of Molecular Biology. 305:567-580.

Lin, H. B., Sun, W., Mosher, D. F., Garcia-Echeverria, C., Schaufelberger, K., Lelkes, P. I. and Cooper, S. L. 1994. Synthesis, surface, and cell-adhesion properties of polyurethanes containing covalently grafted RGD-peptides. Journal of Biomedical Materials Research. 28:329-342.

Liu, S., Sivakumar, S., Sparks, W. O., Miller, W. A. and Bonning, B. C. 2010. A peptide that binds the pea aphid gut impedes entry of Pea enation mosaic virus into the aphid hemocoel. Virology. 401:107-116.

Lopez-Ochoa, L., Ramirez-Prado, J. and Hanley-Bowdoin, L. Peptide aptamers that bind to a geminivirus replication protein interfere with viral replication in plant cells. Journal of Virology. 80:5841-5853.

March, M. and Helenius, A. 2006. Virus entry: open sesame. 2006. Cell. 124:729-740.

Montero-Astúa, M. 2012. Ph.D dissertation. Unveiling and blocking the interaction between Tomato spotted wilt virus and its insect vector, Frankliniella occidentalis. Kansas State University, Manhattan, U. S.

Muhamad, A., Ho, K. L., Basyaruddin Abdul Rahman, A., Tejo, B. A., Uhrin, D. and Tan, W. S. 2015. Hepatitis B virus peptide inhibitors: solution structures and interactions with the viral capsid. Organic and Biomolecular Chemistry. 13:7780-7789.

Oliver, J. E. and Whitfield, A. E. 2016. The genus Tospovirus: emerging bunyaviruses that threaten food security. Annual Review of Virology. 3:101-124.

Pappu, H. R., Jones, R. A. C. and Jain, R. K. 2009. Global status tospovirus epidemics in diverse cropping systems: successes achieved and challenges ahead. Virus Research. 141:219-236.

Pierschbacher, M. D. and Ruoslahti, E. 1984. Cell attachment activity of fibronectin can be duplicated by small synthetic fragments of the molecule. Nature. 309:30-33.

Pierschbacher, M. D. and Ruoslahti, E. 1987. Influence of stereochemistry of the sequence Arg-Gly-Asp-Xaa on binding specificity in cell adhesion. The Journal Biological Chemistry. 262:17294-17298.

Plow, E. F., Pierschbacher, M. D., Ruoslahti, E., Marguerie, G. and Ginsberg, M. H. 1987. Arginylglycyl-aspartic acid sequences and fibrinogen binding to platelets. Blood. 70:110-115.

Pradel, G., Hayton, K., Aravind, L., Iyer, L. M., Abrahamsen, M. S., Bonawitz, A., Mejia, C., Templeton, T. J. 2004. A multidomain adhesion protein family expressed in Plasmodium falciparum is essential for transmission to the mosquito. The Journal of Experimental Medicine. 199:1533-1544.

Riley, D. G, Joseph, S. V., Srinivasan, R. and Stanley, D. 2011. Thrips vectors of tospoviruses. Journal of Integrated Pest Management. 1:1-10.

Rotenberg, D., Jacobson, A., Schneweis, D. J. and Whitfield, A. E. 2015. Thrips transmission of tospoviruses. Current Opinion in Virology. 15:80-89.

Rudolph, C., Schreier, P. H. and Uhrig, J. F. 2003. Peptide-mediated broad-spectrum plant resistance to tospoviruses. Proceedings of the National Academy of Sciences of the United States of America. 100:4429-4434.

Santos, M. J. D., Wigdorovitz, A., Trono, K., Ríos, R. D., Franzone, P. M., Gil, F., Moreno, J., Carrillo, C., Escribano, J. M. Borca, M. V. 2002. A novel methodology to develop a foot and mouth disease virus (FMDV) peptide-based vaccine in transgenic plants. Vaccine. 20:7-8.

Schwab, E. H., Halbig, M., Glenske, K., Wagner, A-S., Wenisch, S., Cavalcanti-Adam, E. A. 2013. Distinct effects of RGD-glycoproteins on integrin-mediated adhesion and osteogenic differentiation of human mesenchymal stem cells. International Journal of Medical Sciences. 10:1846-1859.

Spizz, G. and Blackshear, P. J. 2001. Overexpression of the myristoylated alanine-rich C-kinase substrate inhibits cell adhesion to extracellular matrix components. Journal of Biological Chemistry. 276:32264-32273.

Ullman, D. E., Whitfield, A. E. and German, T. L. 2005. Thrips and tospoviruses come of age: mapping determinants of insect transmission. Proceedings of the National Academy of Sciences of the United States of America. 102:4931-4932.

Wei, Y., Zhang, Y., Cai, H., Mirza., A. M. Iorio, R. M., Peeples, M. E. Niewiesk, S. and Li, J. 2014. Roles of putative integrin-binding motif of the human metapneumovirus fusion (f) protein in cell-cell fusion, viral infectivity, and pathogenesis. Journal of Virology. 88:4338-4352.

Whitfield, A. E. 2004. Ph.D dissertation. Tomato spotted wilt virus acquisition by thrips: the role of the viral glycoproteins. University of Wisconsin-Madison, Madison, U. S.

Whitfield, A. E., Falk, B. W. and Rotenberg, D. 2015. Insect vector-mediated transmission of plant viruses. Virology. 479-480:278-289.

Whitfield, A. E., Kuman, N. K. K., Rotenberg, D., Ullman, D. E., Wyman, E. A., Zietlow, C., Willis, D. K. and German, T. L. 2008. A soluble form of the Tomato spotted wilt virus (TSWV) glycoprotein $G_N$ ($G_N$-S) inhibits transmission of TSWV by *Frankliniella occidentalis*. Phytopathology. 98:45-50.

Whitfield, A. E., Ullman, D. E. and German, T. L. 2005. Tospovirus-thrips interaction. Annual review of phytopathology. 43:459-489.

Whitfield, A. E., Ullman, D. E., German, T. L. 2004. Expression and characterization of a soluble form of Tomato spotted wilt virus glycoprotein $G_N$. Journal of Virology. 78:13197-13205.

Wild, C., Oas, T., McDanal, C., Bolognesi, D. and Matthews, T. 1992. A synthetic peptide inhibitor of human immunodeficiency virus replication: correlation between solution structure and viral inhibition. Proceedings of the National Academy of Sciences of the United States of America. 89:10537-10541.

Woods, A., Couchman, J. R., Johansson, S., Hook, M. 1986. Adhesion and cytoskeletal organization of fibroblasts in response to fibronectin fragments. The EMBO Journal. 5: 665e70.

Xu, Y., Gao, X., Jia, Z., Li, W., Hu, J., Li, Y., Li, Y. and Liu, Y. 2017. Identification of *Taeniothrips eucharii* (Thysanoptera: Thripidae) as a Vector of Hippeastrum chlorotic ringspot virus in Southern China. Plant Disease. 101: 1597-1600.

Yang, M-Y, Sunderland, K. and Mao, C-B. 2017. Virus-derived peptides for clinical applications. Chemical. Reviews. 117:10377-10402.

Yu, Y-P., Wang, Q., Liu, Y-C and Xie, Y. 2014. Molecular basis for the targeted binding of RGD-contain peptide to integrin $α_Vβ_3$. Biomaterials. 35:1667-1675.

Zhang, Z., Pan, L., Ding, Y., Zhou, P., Lv, J. Chen, H., Fang, Y., Liu, X., Chang, H., Zhang, J., Shao, J., Lin, T., Zhao, F., Zhang, Y. and Wang, Y. 2015. Efficacy of synthetic peptide candidate vaccines against serotype-A food-and-mouth disease virus in cattle. Applied Microbiology Biotechnology. 99:1389-1398.

Zhou, J. and Tzanetakis, I. E. 2013. Epidemiology of Soybean vein necrosis-associated virus. Phytopathology. 103: 966-971.

Zhou, J. and Tzanetakis, I. E. 2019. Soybean vein necrosis virus: an emerging virus in North America. Virus Genes. 55:12-21.

Zhou, J., Aboughanem-Sabanadzovic, N., Sabanadzovic, S. and Tzanetakis, I. E. 2018. First report of soybean vein necrosis virus infecting kudzu (*Pueraria montana*) in the United States of America. Plant Disease. 102:1674.

Zhou, J., Kantartzi, S. K., Wen, R.-H., Newman, M., Hajimorad, M. R., Rupe, J. C., Tzanetakis, I. E. 2011. Molecular characterization of a new tospovirus infecting soybean. Virus Genes. 43:289-295.

SEQUENCE LISTING

```
Sequence total quantity: 14
SEQ ID NO: 1            moltype = AA  length = 13
FEATURE                 Location/Qualifiers
source                  1..13
                        mol_type = protein
                        organism = synthetic construct
SEQUENCE: 1
NASIRGDHEV SQE                                                          13

SEQ ID NO: 2            moltype = AA  length = 15
FEATURE                 Location/Qualifiers
source                  1..15
                        mol_type = protein
                        organism = synthetic construct
SEQUENCE: 2
RLTGECNITK VSLTN                                                        15

SEQ ID NO: 3            moltype = AA  length = 13
FEATURE                 Location/Qualifiers
source                  1..13
                        mol_type = protein
                        organism = synthetic construct
SEQUENCE: 3
NASIAAAHEV SQE                                                          13

SEQ ID NO: 4            moltype = AA  length = 13
FEATURE                 Location/Qualifiers
source                  1..13
                        mol_type = protein
                        organism = synthetic construct
SEQUENCE: 4
NASIAGDHEV SQE                                                          13

SEQ ID NO: 5            moltype = AA  length = 13
```

```
FEATURE                 Location/Qualifiers
source                  1..13
                        mol_type = protein
                        organism = synthetic construct
SEQUENCE: 5
NASIRADHEV SQE                                                              13

SEQ ID NO: 6            moltype = AA  length = 13
FEATURE                 Location/Qualifiers
source                  1..13
                        mol_type = protein
                        organism = synthetic construct
SEQUENCE: 6
NASIRGAHEV SQE                                                              13

SEQ ID NO: 7            moltype = AA  length = 15
FEATURE                 Location/Qualifiers
source                  1..15
                        mol_type = protein
                        organism = synthetic construct
SEQUENCE: 7
RLTGECAITK VSLTN                                                            15

SEQ ID NO: 8            moltype = AA  length = 13
FEATURE                 Location/Qualifiers
source                  1..13
                        mol_type = protein
                        organism = synthetic construct
SEQUENCE: 8
NASIAADHEV SQE                                                              13

SEQ ID NO: 9            moltype = AA  length = 13
FEATURE                 Location/Qualifiers
source                  1..13
                        mol_type = protein
                        organism = synthetic construct
SEQUENCE: 9
NASIAGAHEV SQE                                                              13

SEQ ID NO: 10           moltype = AA  length = 13
FEATURE                 Location/Qualifiers
source                  1..13
                        mol_type = protein
                        organism = synthetic construct
SEQUENCE: 10
NASIRAAHEV SQE                                                              13

SEQ ID NO: 11           moltype = AA  length = 6
FEATURE                 Location/Qualifiers
source                  1..6
                        mol_type = protein
                        organism = synthetic construct
SEQUENCE: 11
GRGDSP                                                                       6

SEQ ID NO: 12           moltype = AA  length = 10
FEATURE                 Location/Qualifiers
source                  1..10
                        mol_type = protein
                        organism = synthetic construct
SEQUENCE: 12
RGDSPASSKP                                                                  10

SEQ ID NO: 13           moltype = AA  length = 10
FEATURE                 Location/Qualifiers
SITE                    2
                        note = penicillamine
source                  1..10
                        mol_type = protein
                        organism = synthetic construct
SEQUENCE: 13
GXGRGDSPCA                                                                  10

SEQ ID NO: 14           moltype = AA  length = 5
FEATURE                 Location/Qualifiers
SITE                    4
                        note = D-phenylalanine
source                  1..5
                        mol_type = protein
```

-continued

```
                      organism = synthetic construct
MOD_RES               5
                      note = MeVal
                      note = MeVal
SEQUENCE: 14
RGDFV                                                              5
```

We claim:

1. A composition comprising:

a. a first polypeptide comprising SEQ ID NO: 1 (NASIRGDHEVSQE); and b. a second polypeptide comprising SEQ ID NO: 2 (RLTGECNITKVSLTN).

2. The composition of claim 1, further comprising a feeding buffer, wherein the feeding buffer comprises 8% sucrose and 20% blue food dye.

3. The composition of claim 1, wherein the polypeptides are included in the composition at 10 nM.

4. A construct comprising a polynucleotide encoding at least one of the polypeptides of claim 1 operably connected to a heterologous promoter.

5. The construct of claim 4, wherein the promoter is plant-specific, tissue-specific, or cell-specific.

6. The construct of claim 4, wherein the promoter is temporal, inducible, or constitutive.

7. The construct of claim 4, wherein the construct is a plasmid.

8. The construct of claim 4, wherein the polynucleotide comprises SEQ ID NOs: 1 and 2.

9. A transgenic or genetically-modified plant comprising the construct of claim 4.

10. A cell, seed, part or progeny of the plant of claim 9.

11. A method of inhibiting viral transmission comprising: contacting larvae with the composition of claim 1.

12. A method of inhibiting viral transmission comprising: administering the composition of claim 1 to a plant.

13. A method of inhibiting viral transmission comprising: administering the plant of claim 9 to larvae.

14. The method of claim 11, wherein the larvae is thrips larvae.

15. The method of claim 14, wherein the viral transmission inhibited is from the larvae to the plants.

16. The thrips larvae of claim 14, wherein the thrips is selected from the group consisting of: *Ceratothripoides claratris, T. palmi, F. schultzei, F. occidentalis, F. schultzei, F. occidentalis, F. intonsa, F. gemina, F. intonsa, T. tabaci, T. palmi, Scirtothrips dorsalis, F. fusca, F. bispinosa, T. setosus, F. zucchini, Microcephalothrips abdominalis*, and thrips belonging to the genera *Frankliniella, Thrips, Ceratothripoides, Scirtothrips, Dictyothrips, Neohydatothrips*, and *Taeniothrips.*

17. The method of claim 11, wherein the viral transmission is via an orthotospovirus.

18. The method of claim 17, wherein the orthotospovirus is selected from the group consisting of: tomato spotted wilt virus (TSWV), soybean vein necrosis virus (SVNV), impatiens necrotic spot virus (INSV), bean necrotic mosaic virus (BNMV), capsicum chlorosis virus (CaCV), calla lily chlorotic spot virus (CCSV), chrysanthemum stem necrosis virus (CSNV), groundnut ringspot virus (GRSV), groundnut bud necrosis virus (GBNV), groundnut yellow spot virus (GYSV), iris yellow spot virus (IYSV), melon yellow spot virus (MYSV), peanut bud necrosis virus (PBNV), peanut chlorotic fan virus (PCFV), peanut yellow spot virus (PYSV), tomato chlorotic spot virus (TCSV), tomato yellow fruit ring virus (TYFRV) (=ToVV, tomato varamin virus), tomato necrotic ringspot virus (TNRV), tomato yellow ring virus (TYRV), tomato zonate spot virus (TZSV), watermelon bud necrosis virus (WBNV), watermelon silver mottle virus (WSMoV), zucchini lethal chlorosis tospovirus (ZLCV), polygonum ringspot virus (PolRSV), hippeastrum chlorotic ringspot virus (HCRV), melon yellow spot virus (MYSV), pepper chlorotic spot virus (PCSV), tomato necrotic spot associated virus (TNSaV), groundnut chlorotic fan-spot virus (GCFSV), mulberry vein banding associated virus (MVBaV), and chilli yellow ringspot virus (ChiYRSV).

19. The method of claim 13, wherein the larvae is thrips larvae.

20. The method of claim 16, wherein the viral transmission is via an orthotospovirus.

* * * * *